(12) United States Patent
Zhang et al.

(10) Patent No.: US 6,814,870 B2
(45) Date of Patent: Nov. 9, 2004

(54) MICROCHIP ELECTROSPRAY DEVICE AND COLUMN WITH AFFINITY ADSORBENTS AND USE OF THE SAME

(75) Inventors: Sheng Zhang, Ithaca, NY (US); Xian Huang, Ithaca, NY (US); Thomas N. Corso, Lansing, NY (US); Gary A. Schultz, Ithaca, NY (US); Simon J. Prosser, Ithaca, NY (US)

(73) Assignee: Advion BioSciences, Inc., Ithaca, NY (US)

( * ) Notice: Subject to any disclaimer, the term of this patent is extended or adjusted under 35 U.S.C. 154(b) by 0 days.

(21) Appl. No.: 10/658,008

(22) Filed: Sep. 9, 2003

(65) Prior Publication Data

US 2004/0045904 A1 Mar. 11, 2004

Related U.S. Application Data

(62) Division of application No. 10/078,843, filed on Feb. 19, 2002, now abandoned
(60) Provisional application No. 60/269,973, filed on Feb. 20, 2001.

(51) Int. Cl.$^7$ .............................................. B01D 15/08
(52) U.S. Cl. ................... 210/656; 210/748; 210/198.2; 210/243; 204/450; 250/288; 436/161
(58) Field of Search ................................. 210/656, 748, 210/198.2, 243; 250/288; 204/600, 450; 422/70; 436/161

(56) References Cited

U.S. PATENT DOCUMENTS

| | | |
|---|---|---|
| 4,913,812 A | 4/1990 | Moriguchi et al. |
| 5,045,190 A | 9/1991 | Carbonell et al. |
| 5,240,602 A | 8/1993 | Hammen |
| 5,316,680 A | 5/1994 | Frechet et al. |
| 5,334,310 A | 8/1994 | Frechet et al. |
| 5,431,807 A | 7/1995 | Frechet et al. |
| 5,453,185 A | 9/1995 | Frechet et al. |
| 5,645,717 A | 7/1997 | Hjérten et al. |
| 5,872,010 A | 2/1999 | Karger et al. |
| 5,935,429 A | 8/1999 | Liao et al. |
| 6,048,546 A | 4/2000 | Sasaki et al. |
| 6,238,565 B1 | 5/2001 | Hatch |
| 6,265,168 B1 | 7/2001 | Gjerde et al. |
| 6,596,988 B2 * | 7/2003 | Corso et al. ................ 250/288 |
| 6,627,882 B2 * | 9/2003 | Schultz et al. .............. 250/288 |
| 2004/0035794 A1 | 2/2004 | Zhang et al. |

OTHER PUBLICATIONS

Gale et al., "Small Volume and Low Flow–Rate Electrospray Ionization Mass Spectrometry of Aqueous Samples," *Rapid Commun. Mass. Spectrom.*, 7:1017–1021 (1993).
Gusev et al., "Capillary Columns With in Situ Formed Porous Monolithic Packing for Micro High–Performance Liquid Chromatography and Capillary Electrochromatography," *J. Chromatogr. A*, 855:273–290 (1999).
Hjerten et al., "High–Performance Liquid Chromatography on Continuous Polymer Beds," *J. Chromatogr.*, 473:273–275 (1989).
Nelson et al., "Biosensor Chip Mass Spectrometry: A Chip–Based Proteomics Approach," *Electrophoresis*, 21:1155–1163 (2000).
Merchant et al., "Recent Advancements in Surface–Enhanced Laser Desorption/Ionization–Time of Flight–Mass Spectrometry," *Electrophoresis*, 21:1164–1167 (2000).
Peters et al., "Molded Rigid Polymer Monoliths as Separation Media for Capillary Electrochromatography. 1. Fine Control of Porous Properties and Surface Chemistry," *Anal. Chem.*, 70:2288–2295 (1998).

* cited by examiner

*Primary Examiner*—Ernest G. Therkorn
(74) *Attorney, Agent, or Firm*—Nixon Peabody LLP

(57) ABSTRACT

A microchip-based electrospray ionization device and column with affinity adsorbents is disclosed. The invention includes a microchip array and a capillary tube or alone or attached in combination. At least a portion of the device or column has immobilized affinity adsorbents. Methods for using the device are provided as well for affinity capture of biomolecules to meet the needs for the modem life sciences such as proteomics and drug discover.

19 Claims, 16 Drawing Sheets

① Tube lumen with monolith
② Chip lumen with monolith

Chip inlet side

MICROCHIP ELECTROSPRAY DEVICE AND COLUMN WITH AFFINITY ADSORBENTS AND USE OF THE SAME

This application is a division of U.S. patent application Ser. No. 10/078,843, filed Feb. 19, 2002, now abandoned which claims the benefit of U.S. Provisional Patent Application No. 60/269,973, filed Feb. 20, 2001.

FIELD OF THE INVENTION

The present invention relates to a microchip-based electrospray ionization device and column with affinity adsorbents and a method of using the device and column.

BACKGROUND OF THE INVENTION

Although efforts to evaluate gene activity and to explain biological processes including those of disease processes and drug effects have traditionally focused on genomics in the past two decades, more attention has been paid to proteomics in recent years due to its offering a more direct, complete and promising understanding of the biological functions of a cell. Proteomics research is targeted towards a comprehensive characterization of the total protein complement encoded by a particular genome and its changes under the influence of biological perturbation. Proteomics also involves the study of non-genome encoded events such as the post-translation modification of proteins, interactions between proteins, and the location of proteins within the cell. The study of the gene expression at the protein level is important because many of the most important cellular activities are directly regulated by the protein status of the cell rather than the status of gene activity. Also, the protein content of a cell is highly relevant to drug discovery and drug development efforts since most drugs are designed to target proteins. Therefore, the information gained from proteomics is expected to greatly boost the number of drug targets. Current technologies for the analysis of proteomics are based on a variety of protein separation techniques followed by identification of the separated proteins. Currently, the most popular method for proteomics investigation is the use of high-resolution two-dimensional gel electrophoresis (2D-gel) to map the biological complexity at the molecular level, followed by in-gel proteolytic digestion and sensitive mass spectral techniques to identify the spots. of interest. Complex biological materials typically contain hundreds of biological molecules plus organic and inorganic salts which preclude direct mass spectral analysis. Therefore, significant sample preparation and purification steps are required prior to proteolytic digestion and mass spectral analysis. Although 2-D gel is one of the most powerful methods in the current study of proteomics, this method suffers from the labor-intensive, time consuming, attendant analyte loss and limitation of staining sensitivity to detect the low abundance proteins or peptides. The 2-D gel method suffers from poor reproducibility. In addition, electrophoretic techniques are also plagued by a bias towards proteins of high abundance and the variation of solubility among the complex proteins.

Obviously, there is a need for direct and facile mass spectrometric detection for both major and minor proteins in heterogeneous samples. The significant demands evolving from both the rapid increase of new drug targets and the availability of vast libraries of chemical compounds also apply to the new technologies that can facilitate the screening process.

To avoid the aforementioned disadvantages of the 2-D gel technique, some microchip-based separation devices (arrays) have been developed for rapid analysis of large numbers of samples. Compared to conventional separation columns or devices, microchip-based separation devices (arrays) have higher sample throughput, reduced sample and reagent consumption, and reduced chemical waste. Such devices are capable of fast analyses and provide improved precision and reliability compared to the conventional analytical instruments. The liquid flow rates for microchip-based separation devices range from approximately 1 to 500 nanoliters (nL) per minute for most applications. Capillary electrophoresis (CE) and capillary electrochromatography (CEC) are the two major separation modes used for microchip-based devices. However, liquid chromatography (LC) is not a major separation mode for microchip-based devices and currently is limited to an infusion mode in some limited applications.

Recently, a chip-based proteomics approach has been introduced using biomolecular interaction analysis-mass spectrometry (BIA-MS) in rapidly detecting and characterizing proteins present in complex biological samples at the low- to sub-fmole level (Nelson et al., 2000 *Electrophoresis* 21: 1155–63). One of the most powerful techniques is surface enhanced laser desorption/ionization-time of flight-mass spectrometry (SELDI-TOF-MS) technology which was commercially embodied in Ciphergens's ProteinChip Array System (Merchant et al., 2000 *Electrophoresis* 21: 1164–77). The system (aluminum chip) uses chemically (cationic, anionic, hydrophobic, metal, etc.) or biochemically (antibody, DNA, enzyme, receptor, etc.) treated surfaces for specific interaction with proteins of interest followed by selected washes for SELDI-TOF-MS detection. The power of the. system incorporates straightforward sample preparation with on-chip capture (binding) and detection for protein discovery, protein purification, protein identification from small samples, allowing rapid analysis and assay development on a single platform. Compared to the classic methods of sample purification, the advantages of the Protein Chip system include:

1. on-line "one-step" separation of a small amount of crude biological sources for high throughput analysis;
2. In situ clean-up which diminishes sample loss by eliminating non-specific binding, reducing analyte signal suppression;
3. Pre-concentration of the target molecules, increasing the detection sensitivity particularly for the minor targets compounds.

However, the SELDI-TOF-MS based Protein Chip system suffers from the inability to provide the primary sequencing and structure information for bio-polymers such as proteins and peptides, and for small compounds. It has limitations with respect to the quantitative analysis of analytes. It also has a limited detection level for analytes and limited range of proteins, since only a low number density of analyte is available at any small point on a array spot where the laser beam can hit and generate ions for detection. The detection levels will significantly decline for proteins with a molecular mass above 15–20 Kda.

Electrospray ionization (ESI) provides for the atmospheric pressure ionization of a liquid sample. The electrospray process creates highly-charged droplets that, under evaporation, create ions representative of the species contained in the solution. An ion-sampling orifice of a mass spectrometer may be used to sample these gas phase ions for mass. analysis. Electrospray in front of an ion-sampling orifice of an API mass spectrometer produces a quantitative response from the mass spectrometer detector due to the analyte molecules present in the liquid flowing from the capillary. One advantage of electrospray is that the response for an analyte measured by the mass spectrometer detector is dependent on the concentration of the analyte in the fluid and independent of the fluid flow rate. The response of an analyte in solution at a given concentration would be comparable using electrospray combined with mass spectrometry at a flow rate of 100 $\mu$L/min compared to a flow rate of 100 nL/min. D. C. Gale et al., *Rapid Commun. Mass Spectrom.* 7:1017 (1993) demonstrate that higher electrospray sensitivity is achieved at lower flow rates due to increased analyte ionization efficiency. Thus by performing electrospray on a fluid at flow rates in the nanoliter per minute range provides the best sensitivity for an analyte contained within the fluid when combined with mass spectrometry.

The increasing demand for more efficient and rapid separation techniques in many areas, especially for the pharmaceutical industry, has initiated research towards column consolidation and miniaturization. In recent years, such column consolidation has been achieved when porous polymer continuous beds or monoliths were introduced or invented. Hjertén, *J. Chromatography*, 473 (1989), 273–275 discloses a polymer gel continuous bed prepared by in situ polymerization of an aqueous solution of acrylamide derivatives. Svec and Fréchet disclosed in 1994 and 1995 (U.S. Pat. Nos. 5,334,310 and 5,453,185) a continuous liquid chromatographic column containing a separation medium in the form of a macroporous polymer plug. Column miniaturization has also been achieved when a porous polymer monolith was prepared by radical polymerization in situ in a fused silica capillary. The development of fritless columns with a polymer-based porous monolith rather than conventional spherical beads has become more and more important since it meets the requirement of today's micro-scale liquid chromatography and capillary electrochromatography as described by Peters et al., *Analytical Chemistry*, 70 (1998), 2288–2295; and Gusev et al., J. Chromatography A, 855 (1999), 273–290. It would be desirable to provide a microchip device integrated with the miniaturized and consolidated micro-columns/packings for proteomics research.

In an effort to overcome the above drawbacks to the prior art, the present invention provides a microchip-based ESI device including a miniaturized and consolidated microcolumn and micro-column array having affinity chromatographic adsorbents, which offers higher selectivity and sensitivity, and more accurate qualitative analysis than prior disclosed protein chips and provides quantitative analysis of analytes. The ESI device also offers the capability of providing additional structure and primary sequence information for analytes. In an alternative platform, the microchip device has built-in or attached micro-columns containing an adsorbent in the form of a porous polymer monolith or a coated support. Both platforms and their combinations are used for the detection of complex protein samples and screening of combinatory chemical compounds. In addition, the platforms have potential uses for non-covalent binding in identifying protein-protein, protein-ligand interactions.

SUMMARY OF THE INVENTION

An aspect of the present invention is to develop a microchip-based on-line device for both the affinity capture of biomolecules and the electrospray ionization in coupling with a mass spectrometer.

Another aspect of the invention is to provide a method for using such device for affinity capture of biomolecules to meet the needs for the modern life sciences such as proteomics, drug discovery, clinical diagnostics and forensic science.

A further aspect of the present invention relates to an electrospray device having flow-contacting portions including an affinity chromatographic adsorbent.

A further aspect of the present invention relates to a method for analysis including: providing the electrospray device; and selectively immobilizing affinity ligands on the flow-contacting surface of the device.

A further aspect of the present invention relates to a method for analysis including: providing the electrospray device; selectively binding an analyte on the affinity chromatographic adsorbent by affinity capture; optionally, performing chemical, enzymatic, or physical treatment of the immobilized analyte; selectively desorbing the analyte; electrospraying the desorbed analyte; and passing the electrosprayed analyte to a detector.

A further aspect of the present invention relates to a chromatography column including an affinity chromatographic adsorbent.

According to the invention, these objects have been achieved by a microchip-based electrospray ionization device having an affinity chromatographic absorbent. The device is the combination of a monolithic silicon microchip having a reservoir/nozzle array and a capillary tube/column in communication with one of the chip reservoir. The affinity adsorbent is immobilized in either the chip reservoirs/channels or the capillary tube, or in both. The affinity adsorbent is in the form of either a porous polymer monolith or a surface coating with affinity functions on the flow-contacting surfaces. The affinity chromatography of the present invention includes immobilized metal affinity chromatography (IMAC). The device and its use can achieve the simultaneous affinity capture of biomolecules and subsequent electrospray ionization for mass spectrometry analysis.

DETAILED DESCRIPTION OF THE INVENTION

Figure 1:
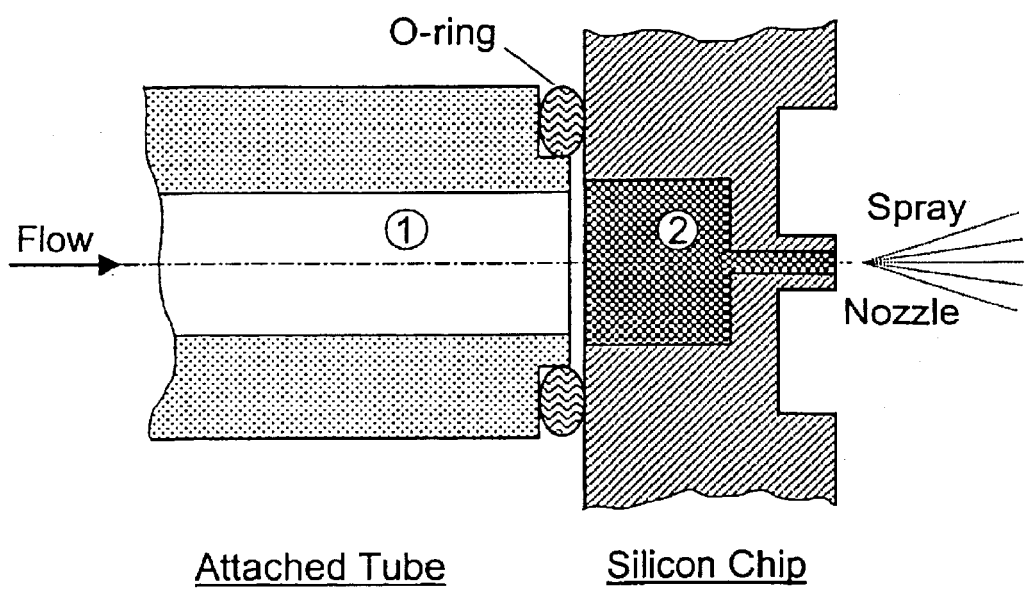
FIG. 1 shows a cross section of a reservoir and its extended nozzle channel of a chip array with the engaged capillary tube. The chip reservoir/channel is packed with a built-in or in situ formed porous polymer monolith, wherein the porous polymer surfaces are immobilized with affinity ligands. There is no immobilized affinity adsorbent in the attached capillary tube.

Electrospray ionization provides for the atmospheric pressure ionization of a liquid sample. The electrospray process creates highly-charged droplets that, under evaporation, create ions representative of the species contained in the solution. An ion-sampling orifice of a mass spectrometer may be used to sample these gas phase ions for mass analysis. When a positive voltage is applied to the tip of the capillary relative to an extracting electrode, such as one provided at the ion-sampling orifice of a mass spectrometer, the electric field causes positively-charged ions in the fluid to migrate to the surface of the fluid at the tip of the capillary. When a negative voltage is applied to the tip of the capillary relative to an extracting electrode, such as one provided at the ion-sampling orifice to the mass spectrometer, the electric field causes negatively-charged ions in the fluid to migrate to the surface of the fluid at the tip of the capillary.

When the repulsion force of the solvated ions exceeds the surface tension of the fluid being electrosprayed, a volume of the fluid is pulled into the shape of a cone, known as a Taylor cone, which extends from the tip of the capillary. A liquid jet extends from the tip of the Taylor cone and becomes unstable and generates charged-droplets. These small charged droplets are drawn toward the extracting electrode. The small droplets are highly-charged and solvent evaporation from the droplets results in the excess charge in the droplet residing on the analyte molecules in the electrosprayed fluid. The charged molecules or ions are drawn through the ion-sampling orifice of the mass spectrometer for mass analysis. This phenomenon has been described, for example, by Dole et al., *Chem. Phys.* 49:2240 (1968) and Yamashita et al., *J. Phys. Chem.* 88:4451 (1984). The potential voltage ("V") required to initiate an electrospray is dependent on the surface tension of the solution as described by, for example, Smith, *IEEE Trans. Ind. Appl.* 1986, IA-22:527–35 (1986). Typically, the electric field is on the order of approximately $10^6$ V/m. The physical size of the capillary and the fluid surface tension determines the density of electric field lines necessary to initiate electrospray.

When the repulsion force of the solvated ions is not sufficient to overcome the surface tension of the fluid exiting the tip of the capillary, large poorly charged droplets are formed. Fluid droplets are produced when the electrical potential difference applied between a conductive or partly conductive fluid exiting a capillary and an electrode is not sufficient to overcome the fluid surface tension to form a Taylor cone.

*Electrospray Ionization Mass Spectrometry: Fundamentals, Instrumentation, and Applications*, edited by R. B. Cole, ISBN 0-471-14564-5, John Wiley & Sons, Inc., New York summarizes much of the fundamental studies of electrospray. Several mathematical models have been generated to explain the principals governing electrospray. Equation 1 defines the electric field $E_c$ at the tip of a capillary of radius $r_c$ with an applied voltage $V_c$ at a distance d from a counter electrode held at ground potential:

$$E_c = \frac{2V_c}{r_c \ln(4d/r_c)} \quad (1)$$

The electric field $E_{on}$ required for the formation of a Taylor cone and liquid jet of a fluid flowing to the tip of this capillary is approximated as:

$$E_{on} \approx \left(\frac{2\gamma\cos\theta}{\varepsilon_o r_c}\right)^{1/2} \quad (2)$$

where $\gamma$ is the surface tension of the fluid, $\theta$ is the half-angle of the Taylor cone and $\epsilon_0$ is the permittivity of vacuum. Equation 3 is derived by combining equations 1 and 2 and approximates the onset voltage $V_{on}$ required to initiate an electrospray of a fluid from a capillary:

$$V_{on} \approx \left(\frac{r_c \gamma \cos\theta}{2\varepsilon_0}\right)^{1/2} \ln(4d/r_c) \quad (3)$$

As can be seen by examination of equation 3, the required onset voltage is more dependent on the capillary radius than the distance from the counter-electrode.

The present invention provides an electrospray device that forms a stable electrospray of substantially all fluids commonly used in CE, CEC, and LC. The surface tension of solvents commonly used as the mobile phase for these separations range from 100% aqueous ($\gamma$=0.073 N/m) to 100% methanol ($\gamma$=0.0226 N/m). As the surface tension of the electrospray fluid increases, a higher onset voltage is required to initiate an electrospray for a fixed capillary diameter. As an example, a capillary with a tip diameter of 14 μm is required to electrospray 100% aqueous solutions with an onset voltage of 1000 V. The work of M. S. Wilm et al., *Int. J. Mass Spectrom. Ion Processes* 136:167–80 (1994), first demonstrates nanoelectrospray from a fused-silica capillary pulled to an outer diameter of 5 μm at a flow rate of 25 nL/min. Specifically, a nanoelectrospray at 25 nL/min was achieved from a 2 μm inner diameter and 5 μm outer diameter pulled fused-silica capillary with 600–700 V at a distance of 1–2 mm from the ion-sampling orifice of an electrospray equipped mass spectrometer.

Electrospray in front of an ion-sampling orifice of an API mass spectrometer produces a quantitative response from the mass spectrometer detector due to the analyte molecules present in the liquid flowing from the capillary. One advantage of electrospray is that the response for an analyte measured by the mass spectrometer detector is dependent on the concentration of the analyte in the fluid and independent of the fluid flow rate. The response of an analyte in solution at a given concentration would be comparable using electrospray combined with mass spectrometry at a flow rate of 100 μL/min compared to a flow rate of 100 nL/min. D. C. Gale et al., *Rapid Commun. Mass Spectrom.* 7:1017 (1993) demonstrate that higher electrospray sensitivity is achieved at lower flow rates due to increased analyte ionization efficiency. Thus by performing electrospray on a fluid at flow rates in the nanoliter per minute range provides the best sensitivity for an analyte contained within the fluid when combined with mass spectrometry.

The present invention provides an electrospray device for integration of microchip-based separation devices with API-MS instruments. This integration places a restriction on the capillary tip defining a nozzle on a microchip. This nozzle will, in all embodiments, exist in a planar or near planar geometry with respect to the substrate defining the separation device and/or the electrospray device. When this co-planar or near planar geometry exists, the electric field lines emanating from the tip of the nozzle will not be enhanced if the electric field around the nozzle is not defined and controlled and, therefore, an electrospray is only achievable with the application of relatively high voltages applied to the fluid.

Control of the electric field at the tip of a nozzle is an important component for successful generation of an electrospray for microfluidic microchip-based systems. This invention provides sufficient control and definition of the electric field in and around a nozzle microfabricated from a monolithic silicon substrate for the formation of multiple electrospray plumes from closely positioned nozzles. The present nozzle system is fabricated using Micro-ElectroMechanical System ("MEMS") fabrication technologies designed to micromachine 3-dimensional features from a silicon substrate. MEMS technology, in particular, deep reactive ion etching ("DRIE"), enables etching of the small vertical features required for the formation of micrometer dimension surfaces in the form of a nozzle for successful nanoelectrospray of fluids. Insulating layers of silicon dioxide and silicon nitride are also used for independent application of an electric field surrounding the nozzle, preferably by application of a potential voltage to a fluid flowing through the silicon device and a potential voltage applied to the silicon substrate. This independent application of a potential voltage to a fluid exiting the nozzle tip and the silicon substrate creates a high electric field, on the order of $10^8$ V/m, at the tip of the nozzle. This high electric field at the nozzle tip causes the formation of a Taylor cone, fluidic jet and highly-charged fluidic droplets characteristic of the electrospray of fluids. These two voltages, the fluid voltage and the substrate voltage, control the formation of a stable electrospray from this microchip-based electrospray device.

The electrical properties of silicon and silicon-based materials are well characterized. The use of silicon dioxide and silicon nitride layers grown or deposited on the surfaces of a silicon substrate are well known to provide electrical insulating properties. Incorporating silicon dioxide and silicon nitride layers in a monolithic silicon electrospray device with a defined nozzle provides for the enhancement of an electric field in and around features etched from a monolithic silicon substrate. This is accomplished by independent application of a voltage to the fluid exiting the nozzle and the region surrounding the nozzle. Silicon dioxide layers may be grown thermally in an oven to a desired thickness. Silicon nitride can be deposited using low pressure chemical vapor deposition ("LPCVD"). Metals may be further vapor deposited on these surfaces to provide for application of a potential voltage on the surface of the device. Both silicon dioxide and silicon nitride function as electrical insulators allowing the application of a potential voltage to the substrate that is different than that applied to the surface of the device. An important feature of a silicon nitride layer is that it provides a moisture barrier between the silicon substrate, silicon dioxide and any fluid sample that comes in contact with the device. Silicon nitride prevents water and ions from diffusing through the silicon dioxide layer to the silicon substrate which may cause an electrical breakdown between the fluid and the silicon substrate. Additional layers of silicon dioxide, metals and other materials may further be deposited on the silicon nitride layer to provide chemical functionality to silicon-based devices.

Mass spectrometry techniques have increasingly played a central role in current proteomics study in terms of their powerful combination of analysis speed, high sensitivity, high selectivity and high accuracy for detecting and identifying proteins including translational modification proteins from a complex sample. The microchip based separation platforms have drawn more attention and are being explored for rapid analysis of a large number of samples from a trace amount of sample available. Recently an electrospray ionization-based monolithic microchip device for mass spectrometry has been developed (Schultz et al., 2000 *Anal Chem* 72: 4058–63). The electrospray device was fabricated from a monolithic silicon substrate using deep reactive ion etching and other standard semiconductor techniques to etch nozzles with 10 micron inner diameter from the planar surface of a silicon wafer. A channel extends through the wafer from the tip of the nozzle to a reservoir etched into the opposite planar surface of the wafer. Each microchip has a 8×12 array of nozzles/reservoirs with a 2.25 mm pitch. The microchip device was demonstrated to have a capability to detect as low as 5 femol tryptic fragments and 1 femol entire protein using direct sample deposition on the chip followed by on-a-fly reconstitution process (Corso, Zhang et al., *Proceedings of the 48th ASMS Conference on Mass Spectrometry and Allied Topics*. Long Beach, Calif. Jun. 11–15, 2000). A stainless mounting bracket was used to hold the microchip and for mounting to the translational stage used for accurate positioning of the microchip array in front of the mass spectrometer ion-sampling orifice.

Suitable electrospray devices and chips and methods for the production thereof are set forth in U.S. patent application Ser. No. 09/748,518, entitled "Multiple Electrospray Device, Systems and Methods," by Schultz et al., filed Dec. 22, 2000, which is herein incorporated by reference in its entirety. Advantages of using an ESI-based microchip array with affinity absorbents include straightforward sample preparation with on-chip capture of trace amount of analytes followed directly by on-line detection. It provides rapid analysis on a single platform and diminished sample loss by in situ clean-up and enhances the detection sensitivity for the low abundant analytes by specifically accumulating the target molecules. The ESI-based chip device offers advantages over a SELDI-TOF-MS based protein chip by its abilities to provide the sequence and structure information for target analytes, and to offer the capability of quantitative analysis. The ESI-chip device can also increase detection sensitivity compared to the SELDI-TOF-MS based device. All the target analytes at each reservoir/nozzle in the ESI chip device remain in a liquid environment and are readily eluted and directed to the mass spectrometer. In addition, the present invention incorporates an additional conductive capillary column with affinity absorbents, which can be engaged to the reservoir of ESI chip array. This combination provides additional flexibility for 1-D affinity separation in the column plus on-line desalting and detection in the ESI chip device. It also provides the capability of 2-D affinity chromatography separation for complex samples.

The following two paragraphs are from column 8, lines 17–55 of U.S. Pat. No. 6,627,882, formally incorporated by reference U.S. patent application Ser. No. 09/748,518:

The present invention relates to an electrospray device for spraying a fluid which includes an insulating substrate having an injection surface and an ejection surface opposing the injection surface. The substrate is an integral monolith having either a single spray unit or a plurality of spray units for generating multiple sprays from a single fluid stream. Each spray unit includes an entrance orifice on the injection surface; an exit orifice on the ejection surface; a channel extending between the entrance orifice and the cut orifice; and a recess surrounding the exit orifice and positioned between the injection surface and the ejection surface. The entrance orifices for each of the plurality of spray units are in fluid communication with one another and each spray unit generates an electrospray plume of the fluid. The electrospray device also includes an electric field generating source positioned to define an electric field surrounding the exit orifice. In one embodiment, the electric field generating source includes a first electrode attached to the substrate to impart a first potential to the substrate and a second electrode to impart a second potential. The first and the second electrodes are positioned to define an electric field surrounding the exit orifice. This device can be operated to generate multiple electrospray plumes of fluid from each spray unit, to generate a single combined electrospray plume of fluid from a plurality of spray units, and to generate multiple electrospray plumes of fluid from a plurality of spray units. The device can also be used in conjunction with a system for processing an electrospray of fluid, a method of generating an electrospray of fluid, a method of mass spectrometric analysis, and a method of liquid chromatographic analysis.

Another aspect of the present invention, is directed to an electrospray system for generating multiple sprays from a single fluid stream. The system includes an array of a plurality of the above electrospray devices. The electrospray devices can be provided in the array at a device density exceeding about 5 devices/cm$^2$, about 16 devices/cm$^2$, about 30 devices/cm$^2$, or about 81 devices/cm$^2$. The electrospray devices can also be provided in the array at a device density of from about 30 devices/cm$^2$ to about 1000 devices/cm$^2$.

The invention includes the combination of a chip array and an attached flow-delivering tube. Either or both of them have an affinity adsorbent in the form of built-in porous polymer monoliths or surface coatings. More particularly, preferred embodiments are described below.

In one embodiment, the present invention provides a microchip-based device (as shown in FIG. 1) which is the combination of a silicon microchip having a reservoir/nozzle array and a capillary tube attached or engaged onto a chip reservoir. The silicon chip is packed with a built-in or in situ formed porous polymer monolith in each of its reservoirs/channels, wherein the porous polymer surfaces are immobilized with affinity ligands. There is no immobilized affinity adsorbent in the attached capillary tube.

Figure 2:
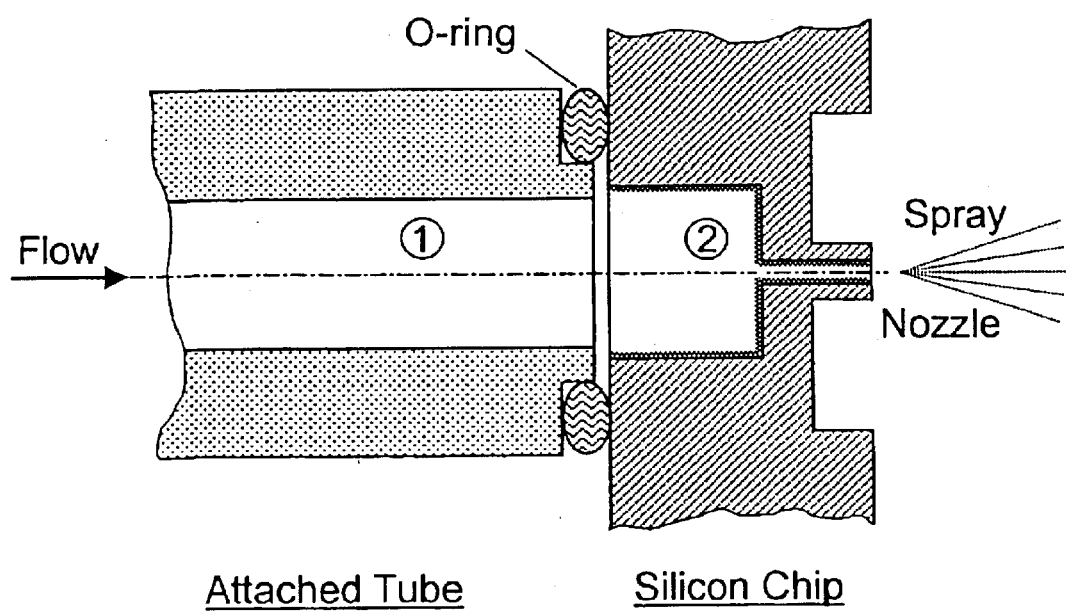
FIG. 2 shows a cross section of a reservoir and its extended nozzle channel of a chip array with the engaged capillary tube. The chip reservoir/channel is coated or immobilized with an affinity adsorbent. There is no immobilized affinity adsorbent in the attached capillary tube.

In a second embodiment, the present invention provides a microchip-based device (as shown in FIG. 2) which is the combination of a silicon microchip having a reservoir/nozzle array and a capillary tube attached or engaged onto a chip reservoir. The silicon chip has affinity adsorbents coated or immobilized on its reservoir/channel surfaces. There is no immobilized affinity adsorbent in the attached capillary tube.

Figure 3:
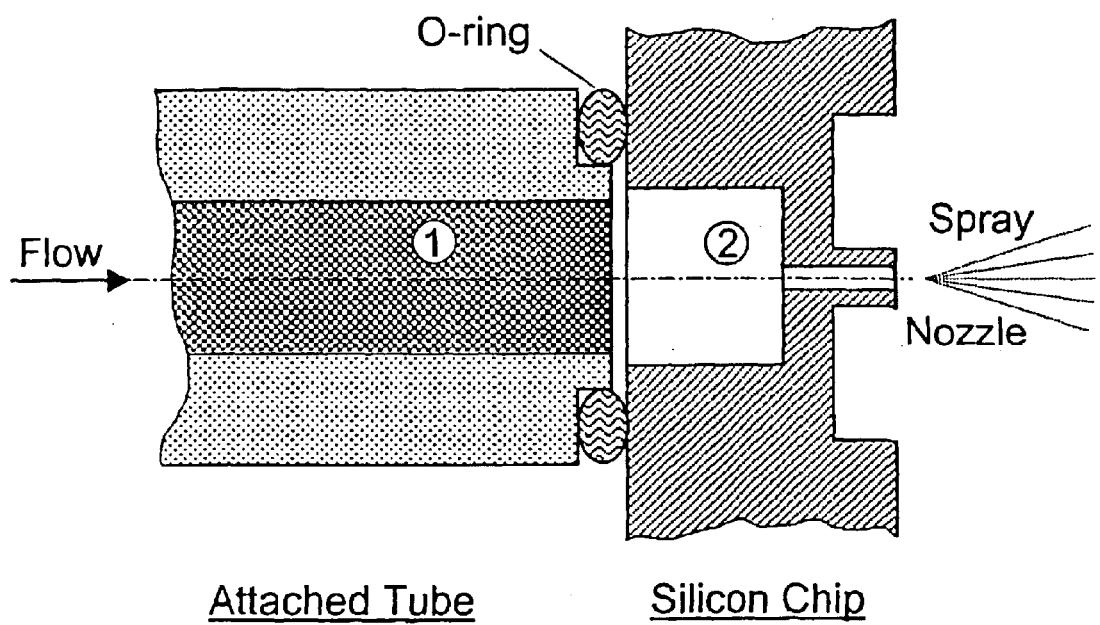
FIG. 3 shows a cross section of a reservoir and its extended nozzle channel of a chip array with the engaged capillary tube. The capillary tube is packed with a built-in or in situ formed porous polymer monolith, wherein the porous polymer surfaces are immobilized with affinity ligands. There is no immobilized affinity adsorbent in the chip reservoir/channel.

In a third embodiment, the present invention provides a microchip-based device (as shown in FIG. 3) which is the combination of a silicon microchip having a reservoir/nozzle array and a capillary tube attached or engaged onto a chip reservoir. The attached capillary tube is packed with a built-in or in situ formed porous polymer monolith, wherein the porous polymer surfaces are immobilized with affinity ligands. There is no immobilized affinity adsorbent in the chip reservoirs/channels.

Figure 4:
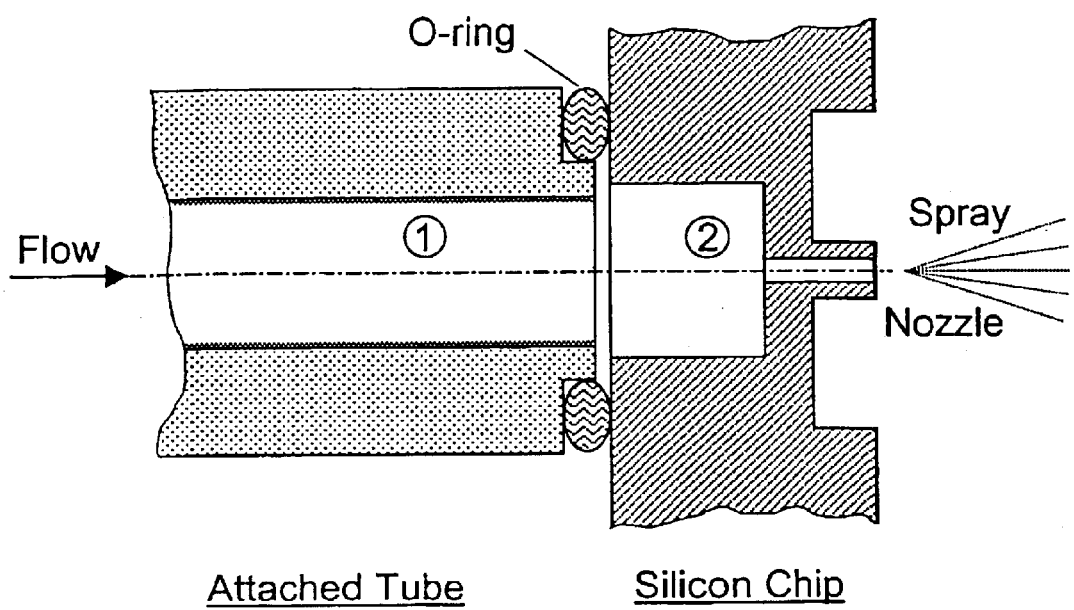
FIG. 4 shows a cross section of a reservoir and its extended nozzle channel of a chip array with the engaged capillary tube. The capillary tube is coated or immobilized with an affinity adsorbent, while the chip reservoir/channel is without an immobilized affinity adsorbent.

In a fourth embodiment, the present invention provides a microchip-based device (as shown in FIG. 4) which is the combination of a silicon microchip having a reservoir/nozzle array and a capillary tube attached or engaged onto a chip reservoir. The attached capillary tube has an affinity adsorbent coated or immobilized on its inner wall. There is no immobilized affinity adsorbent in the chip reservoirs/channels.

Figure 5:
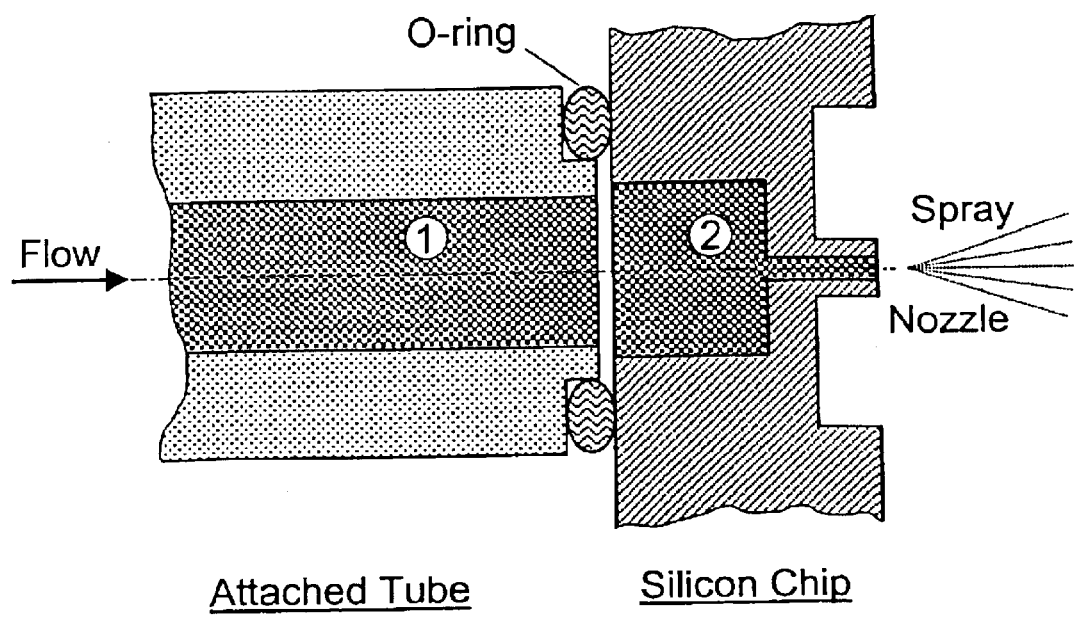
FIG. 5 shows a cross section of a reservoir and its extended nozzle channel of a chip array with the engaged capillary tube. The chip reservoir/channel is packed with a built-in or in situ formed porous polymer monolith. The attached capillary tube is packed with a built-in or in situ formed porous polymer monolith as well. All the porous polymer surfaces are immobilized with affinity ligands.

In a fifth embodiment, the present invention provides a microchip-based device (as shown in FIG. 5) which is the combination of a silicon microchip having a reservoir/nozzle array and a capillary tube attached or engaged onto a chip reservoir. The silicon chip is packed with a built-in or in situ formed porous polymer monolith in each of its reservoirs/channels. The attached capillary tube is packed with a built-in or in situ formed porous polymer monolith as well. All the porous polymer surfaces are immobilized with affinity ligands.

Figure 6:
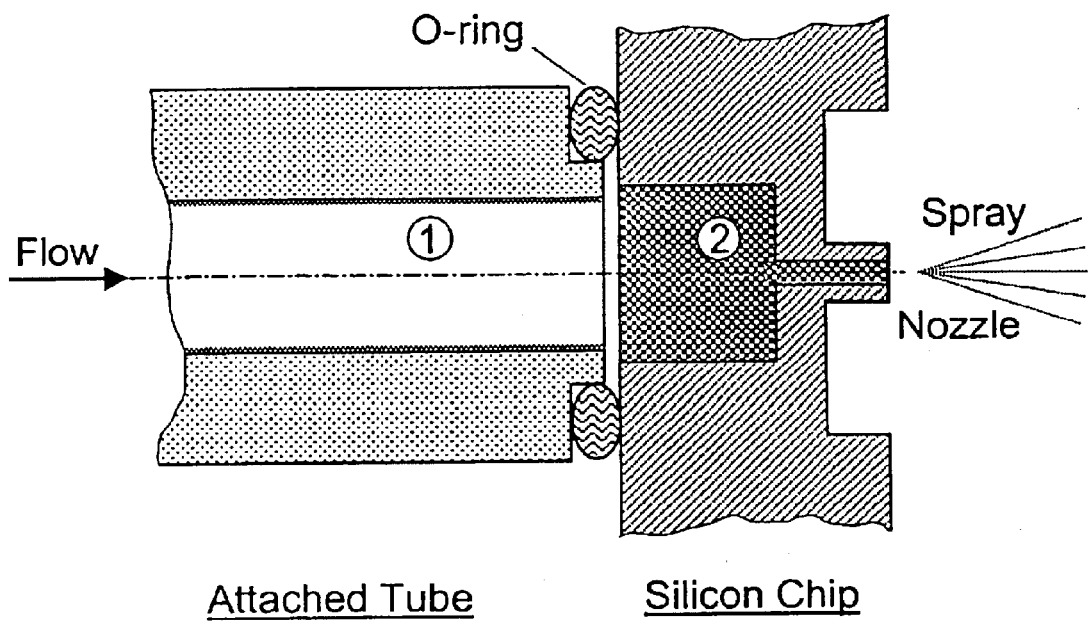
FIG. 6 shows a cross section of a reservoir and its extended nozzle channel of a chip array with the engaged capillary tube. The chip reservoir/channel is packed with a built-in or in situ formed porous polymer monolith, wherein the porous polymer surfaces are immobilized with affinity ligands. The capillary tube is coated or immobilized with an affinity adsorbent.

In a sixth embodiment, the present invention provides a microchip-based device (as shown in FIG. 6) which is the combination of a silicon microchip having a reservoir/nozzle array and a capillary tube attached or engaged onto a chip reservoir. The silicon chip is packed with a built-in or in situ formed porous polymer monolith in each of its reservoirs/channels, wherein the porous polymer surfaces are immobilized with affinity ligands. The attached capillary tube is with an affinity adsorbent coated or immobilized on its inner wall.

Figure 7:
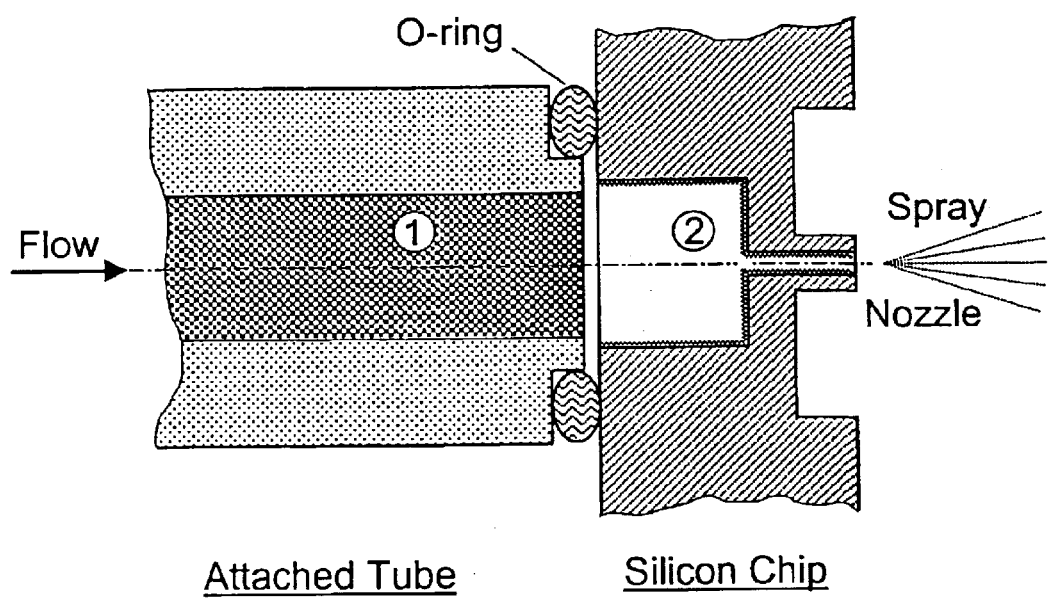
FIG. 7 shows a cross section of a reservoir and its extended nozzle channel of a chip array with the engaged capillary tube. The chip reservoir/channel is coated or immobilized with an affinity adsorbent. The capillary tube is packed with a built-in or in situ formed porous polymer monolith, wherein the porous polymer surfaces are immobilized with affinity ligands.

In a seventh embodiment, the present invention provides a microchip-based device (as shown in FIG. 7) which is the combination of a silicon microchip having a reservoir/nozzle array and a capillary tube attached or engaged onto a chip reservoir. The silicon chip has affinity adsorbents coated or immobilized on its reservoir/channel surfaces. The attached capillary tube is packed with a built-in or in situ formed porous polymer monolith, wherein the porous polymer surfaces are immobilized with affinity ligands.

Figure 8:
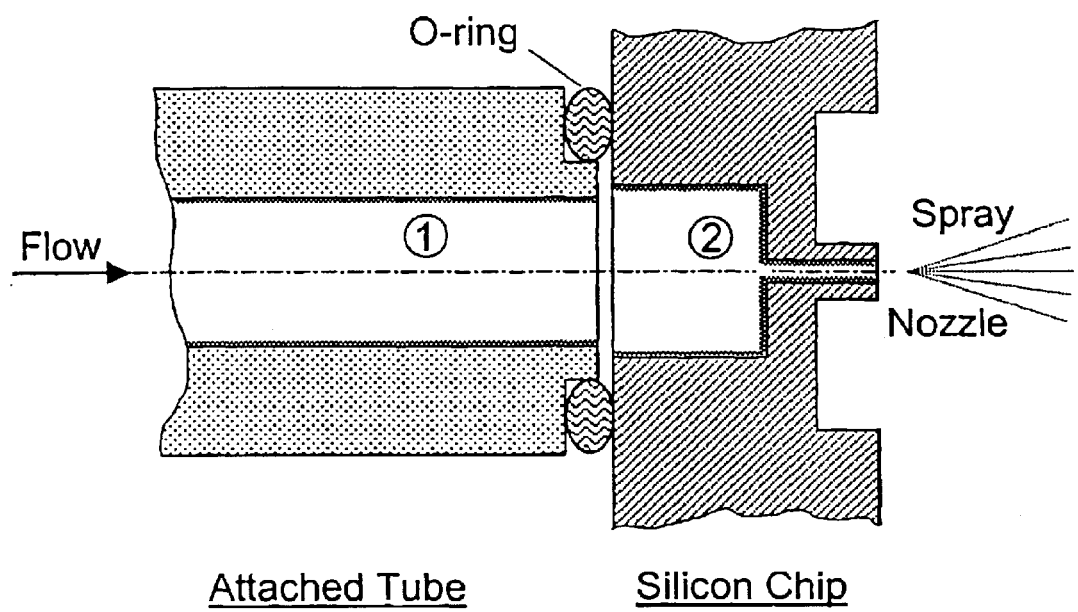
FIG. 8 shows a cross section of a reservoir and its extended nozzle channel of a chip array with the engaged capillary tube. The chip reservoir/channel is coated or immobilized is with an affinity adsorbent. The attached capillary tube also has an affinity adsorbent coated or immobilized on its inner wall.

In an eighth embodiment, the present invention provides a microchip-based device (as shown in FIG. 8) which is the combination of a silicon microchip having a reservoir/nozzle array and a capillary tube attached or engaged onto a chip reservoir. The silicon chip has affinity adsorbents coated or immobilized on its reservoir/channel surfaces. The attached capillary tube also has an affinity adsorbent coated or immobilized on its inner wall.

Figure 9:
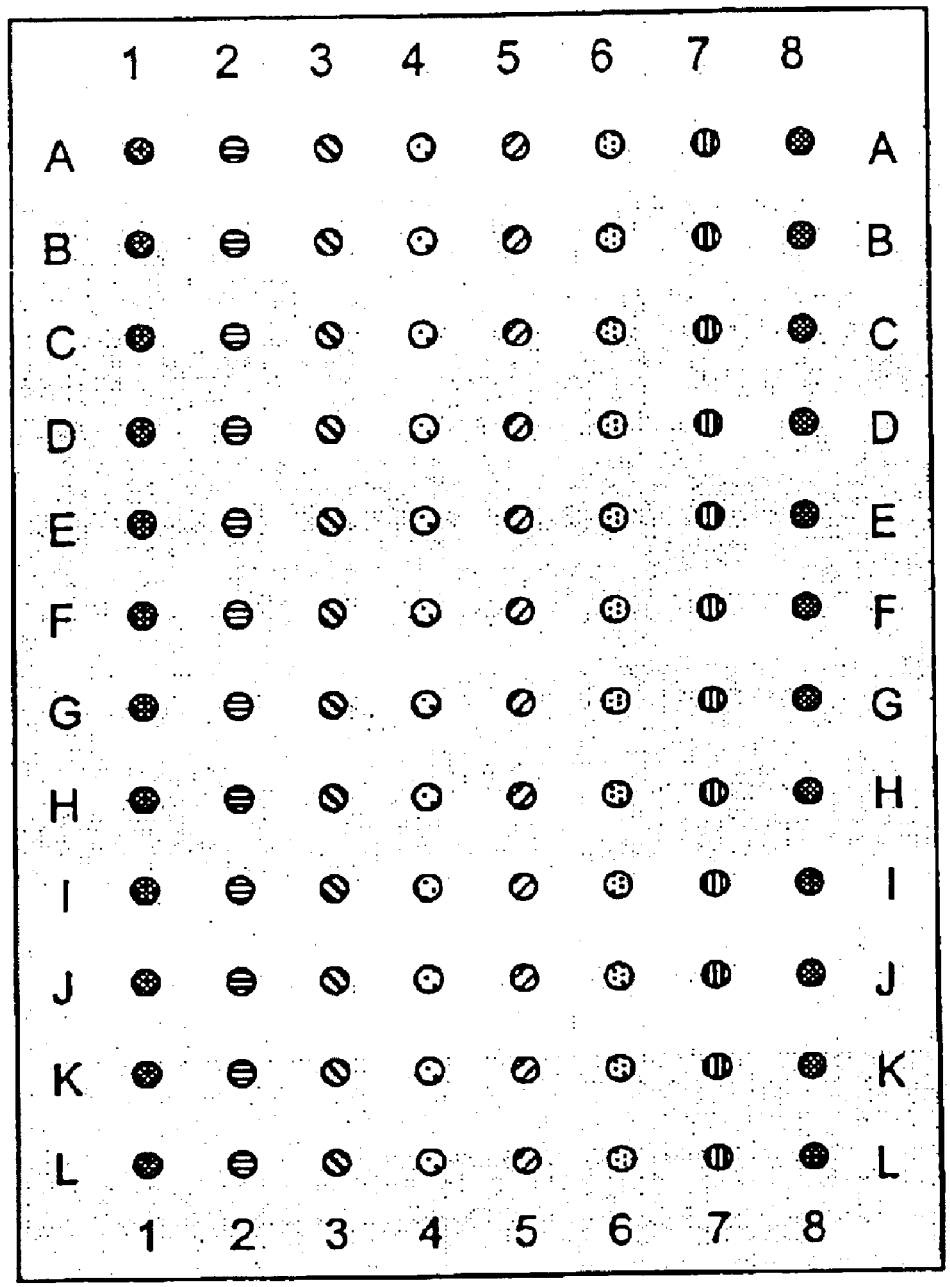
FIG. 9 shows the reservoir-side of the chip with an 8×12 array, wherein the 8 columns (in the vertical direction) have 8 different affinity adsorbents while each column (in the horizontal direction) has the same adsorbent.

In a ninth embodiment, the reservoirs/channels of the silicon chip, as described in the above first, second, fifth, sixth, seventh and eighth embodiments, are immobilized with either one or more than one affinity adsorbents. As a preferred embodiment, FIG. 9 shows the reservoir-side of the chip with an 8×12 array, wherein the 8 columns (in the vertical direction) have 8 different affinity adsorbents while each column (in the horizontal direction) has the same adsorbent. The different affinity adsorbents can be prepared from one support matrix with different affinity ligands. The different affinity ligands can be either structurally/functionally unrelated or structurally/functionally related. For example, the different immobilized ligand molecules can be chemical compounds from the same combinatory library or different protein members from the same protein family or fragments of the different members from the same protein family.

In a tenth embodiment, the attached capillary tube in the device can be provided with or without an adsorbent. If both the attached capillary tube and the chip reservoir/channel array contain affinity adsorbents in one of the configurations (FIGS. 5–8), the immobilized affinity ligand molecules in the attached capillary tube can be either the same or different as that in the chip reservoirs/channels. When the immobilized affinity ligands in the capillary tube and the chip array are different, two-dimensional (2-D) affinity chromatography can be achieved.

In all of the above embodiments, the chip nozzles of the device are used as unique electrospray probes interfaced to a detector, such as, a mass spectrometer for ESI/MS detection. One of the chip nozzles is sequentially positioned to the ion-sampling orifice of the mass spectrometer, and the capillary tube/column is engaged to one reservoir in the backside of the chip.

In all of the above embodiments, the porous polymer monoliths serve as supports for various immobilized affinity ligands. The methods for the preparation of polymer-based capillary monolithic columns for HPLC and capillary electrochromatography can be adapted for use in the present invention. Examples of such polymer monoliths include those covered by U.S. Pat. Nos. 5,334,310 and 5,334,310 (Fréchet and Svec) and introduced by literature like *J. Chromatography A*, 855 (1999), 273–290 (Gusev et al), which are each incorporated herein by reference in their entirety. The processes for preparing such monoliths have been modified at Advion BioSciences, Inc., formerly Advanced BioAnalytical Services, Inc. (Ithaca, N.Y.) based on the company's licensed U.S. patents and other published literature, as set forth herein and suitable monoliths are available from this company.

As a preferred embodiment, the monoliths are in situ formed in the reservoirs/channels or the capillary tube by radical polymerization of monomers in the presence of certain porogen and initiator associated with heat or UV light. The monomers used for polymerization are preferred one or two monovinyl monomers plus a multivinyl monomer (crosslinker). The preferred monovinyl monomers include styrene, vinylbenzyl chloride, vinylacetate, alkyl methacrylates, glycidyl methacrylates. The preferred crosslinkers include divinylbenzene and ethylene glycol dimethacrylate, and the crosslinker's ratio in the total monomer mixture is preferred from about 20 to about 50 v/v %. The porogen can be various solvents or solvent combinations. The preferred porogen is a mixture of a relatively less polar organic solvent (an alcohol, e.g., 1-propanol) and a more polar organic solvent (e.g., formamide). It is preferred that the ratio of monomers to porogen is about 40:60 v/v. The preferred initiators are 2'2-azobisisobutyronitrile and benzoyl peroxide with a concentration in the total polymerizing liquid of from about 0.2 to about 0.5 w/v %. The polymerization is carried out under the preferred conditions of heating at about 45 to about 80° C. for about 8 to about 24 hours with purge of an inert gas when the lumens containing the polymerizing mixture are sealed. With other conditions unchanged, the polymerization can be also carried out at room temperature by UV light at a wavelength of from about 200 to about 400 nm. The resulted porous polymer monoliths have a preferred pore size of about 1 to about 3 µm and porosity of about 45 to about 65 v/v %.

In the present invention, the preferred monoliths are poly(vinylbenzyl chloride-co-divinylbenzene) (PVBC/DVB) with molecular ratio of from about 10 to about 50% divinylbenzene as a crosslinker. The internal pore size distribution and the porosity vary with processes by which the monolith is prepared. The PVBC/DVB monoliths can be either covalently bonded or just physically attached/adhered onto the inner walls of the chip reservoirs/channels and the capillary tube, which is depended on the physical and chemical properties of the wall surfaces. It is important that a monolith formed in the reservoir/channel or a capillary tube be mechanically stable without a gap between the monolith body and its holding surface. A PVBC/DVB monolith covalently bonded in a fused silica capillary can be prepared by first silanizing the internal wall of the capillary with method introduced by Huang and Horváth, *Journal of Chromatography A*, 788 (1997) 155–164.

In all of the above embodiments, the surface coatings on the inner walls of the reservoirs/channels or the capillary tube serve as supports for various immobilized affinity ligands. The chip is silicon with certain surface coating for insulation. Additional coating layers may be applied on it to render the inner walls of the reservoirs/channels compatible with the immobilized adsorbents. The capillary tube is made of fused silica, stainless steel, or various polymers. The internal diameter of the capillary tube is preferred from about 20 to about 380 µm. Those methods for the preparation of inner surface-coated capillaries for HPLC, capillary electrophoresis and capillary electrochromatography can be adapted for use in the present invention. The materials of the coated layer include silica, agarose, and various synthetic polymers. The attachment of the coated layer includes covalent bonding or just physically attached onto the wall of a reservoir/channel or the capillary tube. As a preferred embodiment, the coated layer is in situ formed by radical polymerization of a thin film containing the mixture of monomers and an initiator with heat or UV light. A PVBC/DVB layer covalently bonded in a fused silica capillary can be prepared with the method introduced by Huang et al., *Journal of Chromatography A*, 858 (1999) 91–101. The monomers used for polymerization are preferred one or two monovinyl monomers plus a multivinyl monomer (crosslinker). The preferred monovinyl monomers include styrene, vinylbenzyl chloride, vinylacetate, alkyl methacrylates, glycidyl methacrylates. The preferred crosslinkers include divinylbenzene and ethylene glycol dimethacrylate, and the crosslinker's ratio in the total monomer mixture is preferred from about 20 to about 50 v/v %. It may be not necessary to add a porogen into the mixture. The preferred initiators are 2'2-azobisisobutyronitrile and benzoyl peroxide with a concentration in the total polymerizing liquid of from about 0.2 to about 0.5 w/v %. The polymerization is carried out under the preferred conditions of heating at from about 45 to about 80° C. for about 8 to about 24 hours with purge of an inert gas when the lumens containing the polymerizing mixture are sealed. With other conditions unchanged, the polymerization can be also carried out at room temperature by UV light at a wavelength of from about 200 to about 400 nm. The resulted polymer coated layer has a preferred thickness of less than about 5 µm. In some cases, the capillary inner wall can be covalently bonded or physically attached with materials other than the in situ formed synthetic vinyl polymers as the supports. The affinity ligand molecules can be directly bonded onto the tube inner wall when the wall surface is chemically active for such bonding, which simplifies the coating procedure but usually results a low surface capacity for affinity capture.

In all of the above embodiments, all of the supports in the form of porous polymer monoliths and coatings have various immobilized affinity functions on their surfaces. The methods for the grafting or immobilizing various affinity functions onto different support surfaces to make stationary phases for affinity liquid chromatography including immobilized metal affinity chromatography (IMAC) can be adapted for use in the present invention. Methods for immobilizing affinity functions are varied and dependent on the chemistry of the ligand itself, and whether a spacer arm is required. As a preferred embodiment, the immobilized ligand molecules are chosen from organic compounds, inhibitors, biotins, proteins, peptides, enzymes, coenzymes, receptors, affinity tags, nucleic acids, antibodies, carbohydrates, lectins, dyes and protein surface domains involved in molecular recognition. Preferred immobilized ligands include a potential drug candidate or a mixture with potential drug candidates from a combinatorial compound library as an example of organic compounds, benzamidine as an example of inhibitors, D-biotin or biotinylated molecules as an example of biotins, Avidin or Protein A as an example of proteins. Preferred immobilized ligands also include antisense peptides (eg. antisense Arg-vasopressin peptide) as an example of peptides, trypsin as an example of enzymes, adenosine 5'-monophosphate (5'-AMP) as an example of coenzymes, Interleukin-2 receptor as an example of receptors, polyamino acids (eg. polyhistidine) as an example of affinity tags, histidine or lysine as an example of amino acids, a fragment of calf thymus DNA as an example of nucleic acids, sheep anti-rabbit IgG as an example of antibodies, monosaccharide or its derivatives as an example of carbohydrates, concanavalin A (Con A) as an example of lectins and Cibacron Blue F3G-A as an example of dyes. In another preferred embodiment, metal ion chelating ligands, such as iminodiacetic acid (IDA), nitrilo triacetic acid (NTA), and tris(carboxymethyl) ethylene diamine (TED), are immobilized on the supports. These chelating ligands bind tightly to metal ions, in particular to the divalent ions, such as, Ni(II), Cu(II), Zn(II), Co(II), Ca(II) and Mg(II) and trivalent ions, such as, Fe(III) and Ga(III). The structure of the chelating ligand is such that a metal ion, once bound, does not have all its coordination sphere occupied. These spare coordination sites are weakly occupied by water or buffer molecules, which can be then replaced by more strongly complexing sites on proteins, antibodies, or other affinity molecules.

In all of the above embodiments, the invention presents a method for using the device. In a preferred embodiment, the liquid in the inlet of the capillary tube/column is connected to the mass spectrometer high voltage power supply, while the chip (with insulation coating on its all silicon surfaces) is connected on its silicon body to the ground of the high voltage power supply. A micro pump is used to deliver liquid to the device capillary tube/column inlet through a nonconductive capillary. Other liquid delivering systems such as small vials with gas pressure or various syringe pumps can also be used. Samples can be loaded into the capillary tube/column through the liquid-delivering system with or without automatic operation.

In a further embodiment, the present invention provides a method for using the device for affinity binding of target analyte molecules. The target analytes in unfractionized samples are optimized for specifically binding to the immobilized adsorbents in the device. The optimized solution condition not only provides good solubility for the desired analytes but also greatly facilitates the affinity interaction (chemically or biochemically binding or physically adhere) between the mobile phase and stationary phase. Generally, the flow-contact surfaces with or without immobilized affinity functions are equilibrated with the optimized solution prior to the loading of the unfractionated samples.

The affinity adsorbents of the present invention can be applied to affinity chromatography columns and micro columns in accordance with the processes disclosed herein. In another embodiment, the present invention includes a method to enable the successful desorption of the docked interesting analytes on the flow-contacted surfaces in both the attached tube/column and the chip array, or in either of them. Typically, after crude samples are loaded, the flow-contacted surfaces are washed completely with the aforementioned optimized solution. If multiple sample loading is necessary, repeating washing steps can be applied for those low abundant targets. The captured targets are desorbed and eluted with either an organo-aqueous solution or a buffer with extremely high or low pH or both. Alternatively, the captured targets are also desorbed and eluted with the loading buffer containing a competitor compound or reducing agents such as cysteine, mercapethanol and DTT. The solution containing the eluted targets exits the device from the nozzle channel for ESI/MS or ESI/MS/MS detection. Small compounds and peptides can be directly detected and identified by MS/MS analysis. When the attached capillary tube is just an open tube without an adsorbent (FIGS. 1 and 2) and the chip array has multiple affinity adsorbents in each row or column (FIG. 9), the device can be used for multiple analyses of one or more analytes, where the loading and elution conditions vary among different rows or columns. Usually the multiple loading of the crude samples can help detect and identify those very low abundant analytes. During the loading and washing steps, the excess waste solution can be blotted out by Whatman paper applied in nozzle side to avoid the potential cross contamination in the subsequent ESI/MS analysis through the nozzles. For each row or column of the adsorbents, differential elution from less stringency to more stringency is orderly performed for increasing the selectivity threshold. As a result of this differential elution, compounds or macromolecules with shared similar physical, chemical and biochemical properties are retained on the active surfaces of the adsorbents in the chip reservoirs/channels under less stringent wash and elution for ESI/MS detection. Only specific analytes with strong surface affinity to the immobilized adsorbents are enriched and eluted by the stringent conditions. This differential elution is useful for investigating a variety of purification conditions on multiple active surfaces and particularly useful for screening combinatory chemical compounds and identifying the different protein or peptide members from the same protein or peptide family.

In another embodiment, the present invention includes a method for on-line chemical, enzymatic and physical treatment of the captured analytes. After the interest analytes are bound on the flow-contacting surfaces of the device, an alternative way to further characterize the bound analytes is to perform a serial of different chemical, biochemical or physical modifications before elution. Followed by washing steps to further remove a portion of the modified analytes, the remaining portion of the analytes bound to the adsorbents is then eluted for ionization and electrospray through a nozzle of the microchip device. This post-capture on-line modification for the interest analytes provides not only an additional confirmation for identifying the analytes but also a direct evidence of elucidating primary, secondary, tertiary or quaternary structure of the analytes and their components. For instance, if a phosphorylated protein is bound through its phosphorous groups chelated on the adsorbents in one row/column of the chip array, the elution of the whole protein followed by ESI/MS analysis will yield little information for the identification of the analytes. However, the different reservoirs containing the same affinity adsorbent in one row/column of the chip can serve as multiple micro-columns for different purposes. For example, one such protein-loaded "multiple micro-columns" can be used for on-line proteolysis digestion when the endoprotease digestion solution is delivered by the engaged capillary tube. A direct detection of the resulting peptides mapping combining with sequencing one of the selected peptide by ESI/MS/MS will result in unambiguously identifying the protein. Alternatively, after a washing step to wash away unbound peptides, a further treatment with and without phosphatase for the remaining peptide(s) containing a phosphorous group followed by desorption and analysis of the remaining peptides will yield information on a site-specific location of the phosphorous groups. Besides the phosphorylation modification, the method can also be used to verify several types of the sequence-specific post-translational modifications including dephosphorylation, glycosylation, cysteine residue reactivity, site-specific modifications (such as histidine residues), and ligand binding.

An additional embodiment of the present invention includes a method for separation of classes of target analytes by two-dimensional affinity chromatography. As shown in FIGS. 5–8, the 2-D columns are provided by the combination of the capillary column and the chip array. Such 2-D affinity separation mode provides a potential option for efficiently characterizing the structural closely related analytes. Typically, the capillary column contains the adsorbent less specific or suitable for binding of a serial similar analytes, while the chip array contains the adsorbents more specific or suitable for secondary affinity separation of the retained classes of analytes.

Another embodiment of the present invention also includes a microchip-based device and a method for 2-D separation of chemical compounds and biomolecules. The device is the combination of a silicon microchip having a reservoir/nozzle array and a capillary tube attached onto a chip reservoir. The attached capillary tube is packed with a built-in or in situ formed porous polymer monolith. The polymer surface is covalently immobilized with ion-exchange groups (such as $SO_3^-$, $CO_2^-$, $NR_3^+$ and DEAE). The silicon chip is packed with a built-in or in situ formed porous polymer monolith in each of its reservoirs/channels. The porous polymer monolith surfaces are covalently bound with alkyl groups $C_4$–$C_{18}$. Therefore, the capillary column serves as an ion-exchange column to separate the mixture sample based on the charge states of the molecules, while the silicon chip acts as hydrophobic adsorption columns for both sample cleanup and electrospray ionization. The effluents containing the separated target molecules under stepwise elution with different concentrations of the counter-ions (salts) are delivered to the reservoir array from low to high concentrations of counter-ions. As a result, the separated molecules in different reservoirs of the microchip are elctrosprayed and identified by ESI/MS.

One aspect of the invention provides a device and a method for screening, detecting and identifying a plurality of proteins or peptides for their ability to bind to a particular component of a sample. Such proteins or peptides are in low abundance, hard to be detected and identified by conventional 2-D gel coupled with mass spectrometry system. Such proteins or peptides are either post-translationally modified or unmodified. Such proteins or peptides are capable of involving macromolecule recognition for structural higher order and functional supramolecular assemblies. The proteins and peptides are biomarkers which are up or down-regulated in response to a particular physiological or pathological state.

Another aspect of the invention provides a device and a method for use in a diagnostic and forensic manner when the plurality of analytes being assayed is indicative of a disease condition or the presence of 'marker' molecules or the presence of pathogen in an organism.

An additional aspect of the invention may be used for drug screening when a potential drug candidate is screened directly for its ability to bind or otherwise interact with a plurality of proteins. And also a plurality of potential drug candidates are screened for their ability to bind or interact with one or more immobilized proteins (such as receptors, enzymes and antibodies).

The present invention is further described in the following Examples, which are recited herein as illustrative of the present invention but in no way limit the present invention.

EXAMPLE 1

Figure 10:
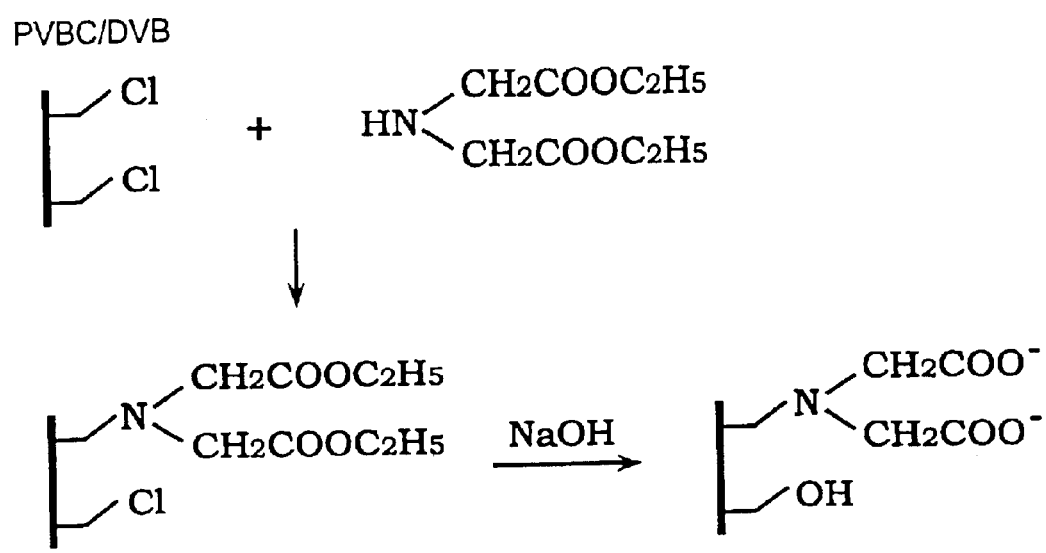
FIG. 10 is a scheme for the surface modification of a porous poly(vinylbenzyl chloride-co-divinylbenzene) (PVBC/DVB) monolith or a coated PVBC/DVB layer in a capillary tube or a chip reservoir/channel in Example 1, which results in the surface chemistry suitable for immobilized metal affinity chromatography (IMAC).

This example includes a procedure for the surface modification of a porous PVBC/DVB monolith or a coated PVBC/DVB layer in a capillary tube or a chip reservoir/channel, resulting the surface chemistry suitable for immobilized metal affinity chromatography (IMAC). As shown in FIG. 10, the surface of the PVBC/DVB support is reacted with diethyl iminoacetate, followed by the hydrolysis with aqueous sodium hydroxide solution.

A solution of 20%(v/v) diethyl iminodiacetate (DIDA) in acetonitrile is prepared and degassed with helium bubbling. The solution is filled into the capillary tube and the chip reservoirs/channels with PVBC/DVB support. The chip reservoirs/channels and the capillary tube are then sealed. The chip can be also submerged in the solution in a closed container. Subsequently, they are placed in an oven and heated at 80° C. for 24 hours. After the solution is removed from the chip and the capillary tube, they are washed with acetonitrile and water. By the same way, they are then filled with or put into a solution of 1 M NaOH and heated in the oven again at 80° C. for 16 hours. They are finally washed with water, methanol, 0.1 M HCl and water respectively.

EXAMPLE 2

Figure 11:
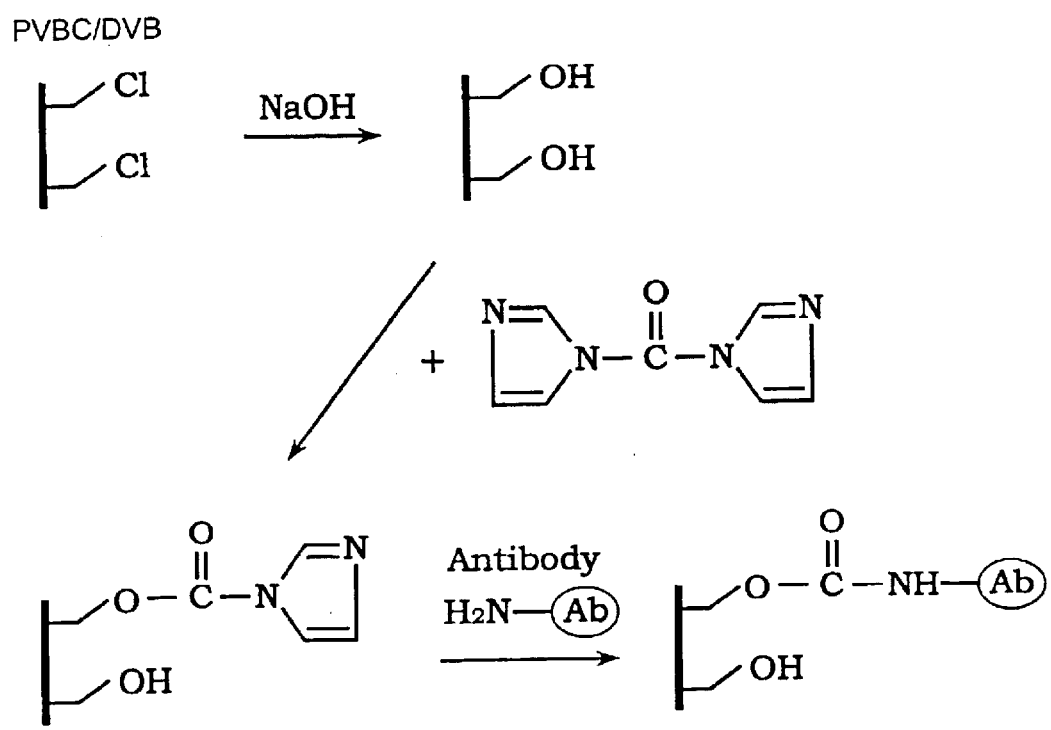
FIG. 11 is a scheme for the surface modification of a porous PVBC/DVB monolith or a coated PVBC/DVB layer in a capillary tube or a chip reservoir/channel in Example 2, which results in the surface chemistry suitable for affinity chromatography.

This example includes a procedure for the surface modification of a porous PVBC/DVB monolith or a coated PVBC/DVB layer in a capillary tube or a chip reservoir/channel, resulting in a surface chemistry suitable for affinity chromatography. As shown in FIG. 11, the surface of the PVBC/DVB support is hydrolyzed with aqueous sodium hydroxide solution to provide a hydroxyl group enriched hydrophilic surface, followed by a procedure from a published method for the activation of crosslinked agaroses (Bethell et al., *The Journal of Biological Chemistry*, 254 (8) (1979) 2572–2575) as modified below.

An aqueous solution of 1 M NaOH is filled into the capillary tube and the chip reservoirs/channels with PVBC/DVB support. The chip reservoirs/channels and the capillary tube are then sealed. The chip can be also submerged in the solution in a closed container. Subsequently, they are placed in an oven and heated at 80° C. for 24 hours. After the solution is removed from the chip and the capillary tube, they are thoroughly washed with water and water-free acetonitrile.

The hydrolyzed PVBC/DVB surfaces are treated with freshly prepared acetonitrile solution containing 5%(w/v) 1,1'-carbonyldiimidazole (CDI) at room temperature for 30 minutes. After it is washed with acetonitrile again, the surfaces are reacted at 4° C. overnight with a certain concentration of antibodies or other affinants in water at pH 10. The antibodies or other affinants have the primary amine functions so that the affinants can be covalently coupled on the CDI activated PVBC/DVB surfaces.

EXAMPLE 3

The following includes applications for using the device with affinity adsorbents including immobilized iminodiacetic acid and subsequent metal ions prepared in EXAMPLE 1.

Figure 12:
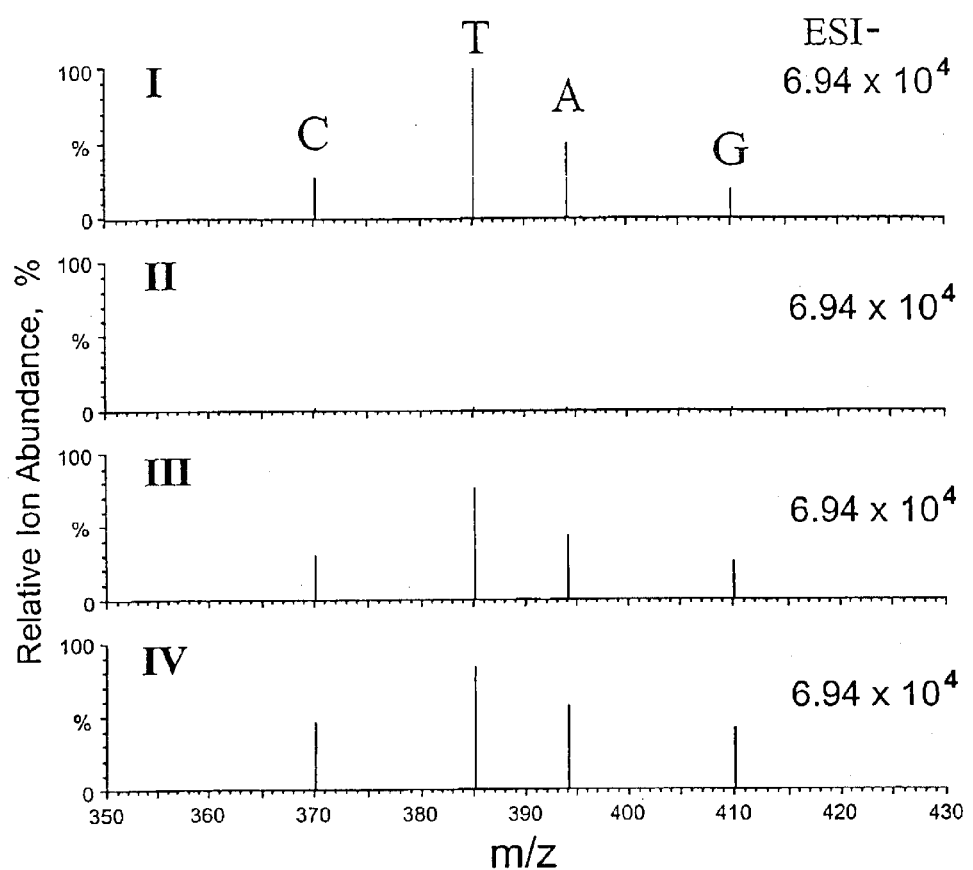
FIG. 12 shows the selected reaction monitoring (SRM) MS/MS mass spectra of dideoxynucleotides (ddNTPs) samples in EXAMPLE 3 that are pretreated with and without a porous polymer monolith immobilized with an iminodiacetic acid group.

1. Mg(II) ions are chelated by iminodiacetic (IDA) groups immobilized in the surfaces of a porous polymer monolith as described above. The following 1 µM ddNTPs samples with or without 2 mM Mg(II) was used for initially testing if home-made IDA immobilized micro column or microchip device functions properly and for testing the binding capacity of the apparatus. A 12 cm length with 180 µm id monolith IDA column was connected to a triple quadrupole Micromass Quattro II (Cheshire, U.K.) mass spectrometer and the column was equilibrated with a mobile phase 50% methanol-0.1% acetic acid. A 10 µL mixture of 1 µM ddNTPs and 2 mM Mg(Ac)$_2$ was injected into the column through an auto-sample injector. The mobile phase was delivered to the mass spectrometer probe at flow rate of 30 µL/min. The ddNTPs were passed through the column and detected by mass spectrometer. The mass spectrometer was equipped with a Z-spray source and operated in negative ion MS/MS selected reaction monitoring (SRM) mode. The Z-spray desolvation temperature and capilliary voltage were 400° C. and 3000V respectively. The collision energy was 35V and the dwell time for each transition was 200 ms. The following SRM transitions were monitored for each of the ddNTP bases: ddCTP, m/z 370.1→m/z79.0; ddTTP, m/z 385.1→m/z79.0; ddATP, m/z 394.1→m/z79.0; ddGTP, m/z 410.1→m/z79.0. FIG. 12 shows the SRM MS/MS mass spectra of ddNTPs samples. The ddNTPs sample containing Mg(II) without treatment with IDA micro column prior to ESI/MS analysis showed that ddNTPs transition ions were significantly suppressed by the presence of Mg(II) ion (as shown in FIG. 12 II) while the same samples treated with IDA immobilized porous polymer gave the same signal intensity of the ddNTPs transition ions (FIG. 12 IV) compared to the standard ddNTPs sample (in the absence of Mg(II), FIG. 12 I) and the sample treated with immobilized IDA gel from PIERCE (FIG. 12 III). This suggests that the Mg(II) in the reaction solution was chelated to the monolith surface of the micro column. The binding capacity of the above column to Mg(II) under above condition is 2 mmoles per mL of porous polymer monolith bed volume.

Figure 13:
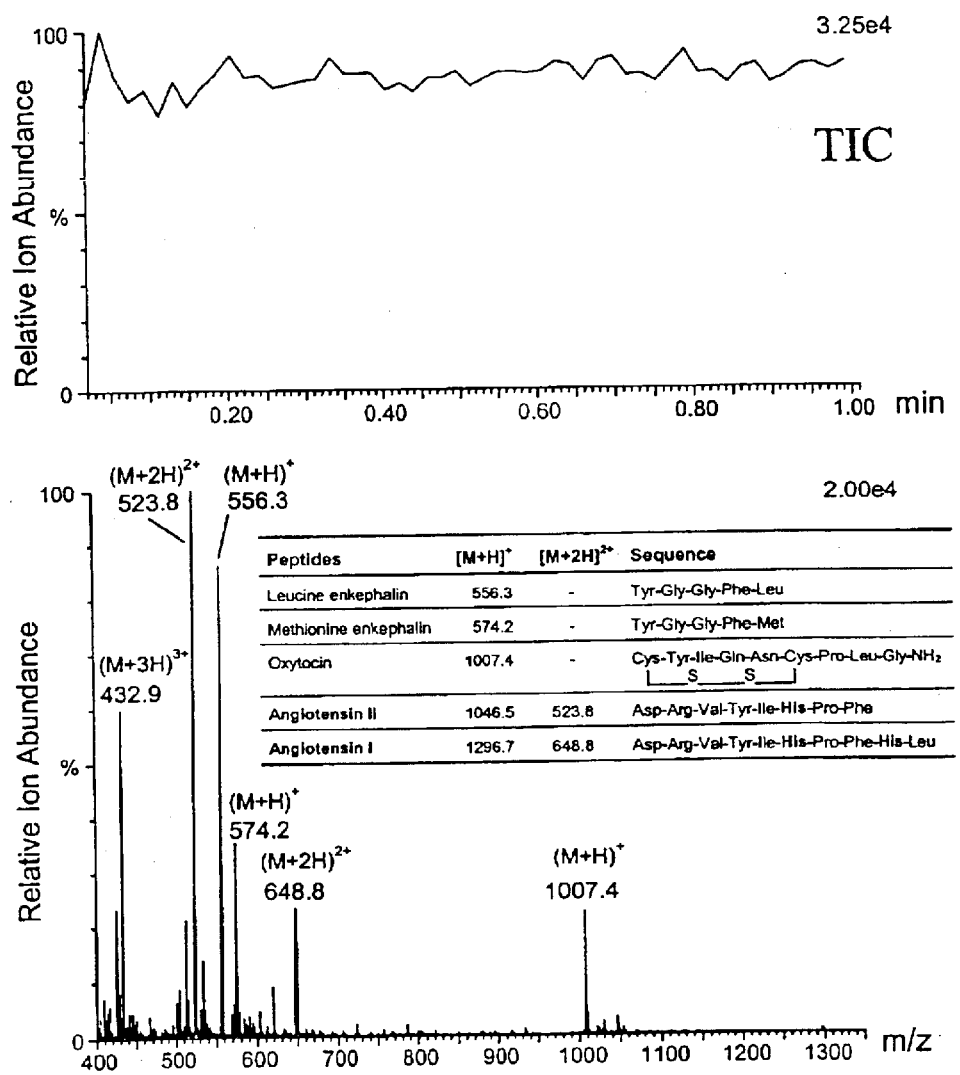
FIG. 13 shows a mass spectrum of the infusion of a five-peptide mixture (1 $\mu$M each component) in 50% methanol/50% water with 0.1% acetic acid through a microchip electrospray device and serves as a control. The top panel shows the total ion current (TIC) over the 1-min acquisition and the bottom shows the mass spectrum of five-peptide mixture resulting from summing the 1-min data. The inset displays the amino acid sequences of five peptides used in this study.
Figure 14:
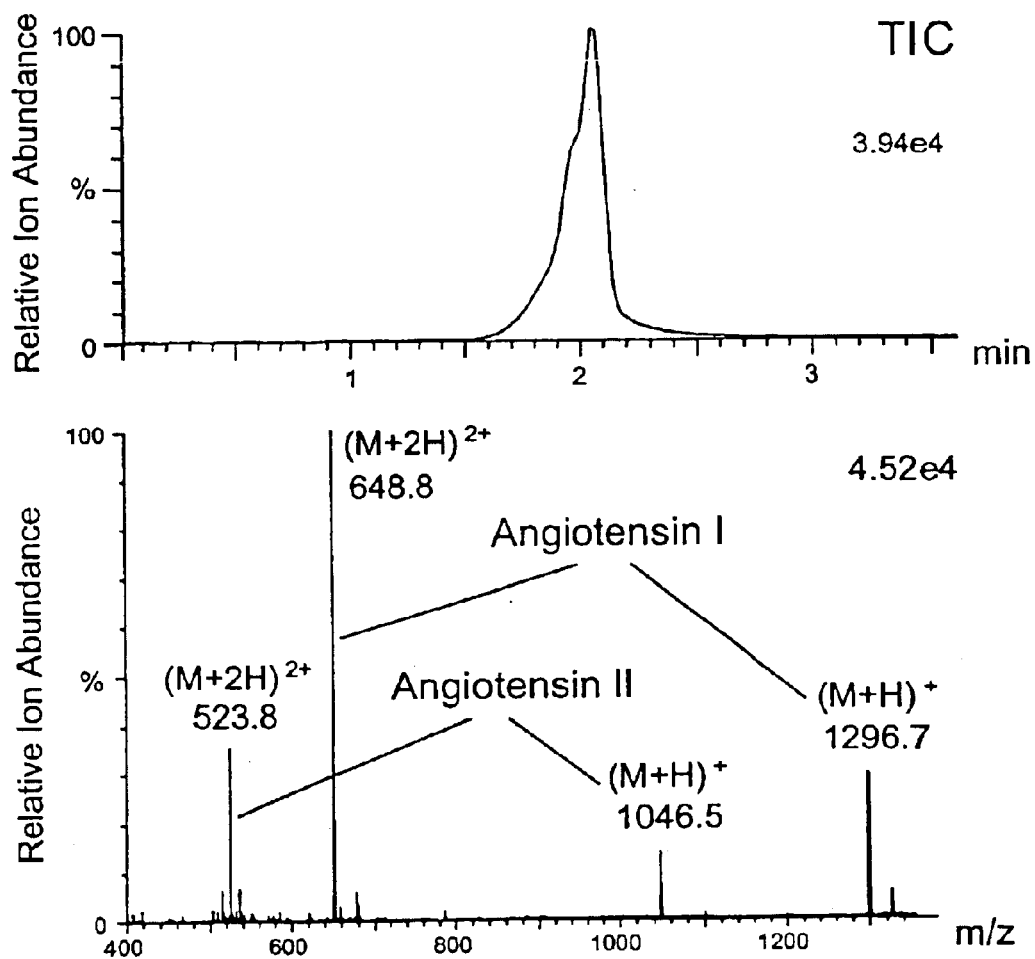
FIG. 14 shows a mass. spectrum of the results of a five-peptide mixture (1 pmol of each component) loaded on an iminodiacetic acid (IDA)-immobilized monolith PEEK column (381 $\mu$m I.D.×4.7 cm), eluted directly to a stainless steel column (125 $\mu$m I.D.×10 cm) containing the poly(styrene- co-divinylbenzene) (PS-DVB) monolith followed by on-line gradient elution from 5–50% acetonitrile with 0.1% acetic acid in 10 minutes through a microchip electrospray device. The top panel shows the TIC chromatogram of the gradient elution over 3.5-min acquisition. The bottom panel displays the mass spectrum of elution components resulting from summing the 3.5-min data.

2. Cu(II) ions are chelated by IDA in both capillary column and microchip device for affinity capture of his-rich peptides, proteins and Lectins (ConA). Initially the above monolith IDA column was tested. A 381 μm I.D.×4.7 cm monolith IDA column was connected to a micro pump system and to a Micromass LCT-TOF-MS (Cheshire, U.K.) mass spectrometer for ESI/MS detection. The column was pre-charged with Cu(II) by injection of 100 μL of 40 mM $Cu(Ac)_2$. The excess of Cu(II) in the column was removed with distilled water and the column was equilibrated with 100 μL of 1M NaCl. A mixture of synthetic peptides containing 1 pmole of each angiotensin I (1295.7 Da), Angiotensin II (1045.5 Da), Leu-enkephalin (555.3 Da), Met-enkephalin (573.2 Da) and Oxytocin (1006.4 Da) in equilibration buffer was loaded into the column. The column was then washed with 1 M NaCl and connected to the PS-DVB monolith stainless column with 10 cm length and 125 μm id used for engaging the ESI microchip reservoir. The bound peptides were then eluted from the IDA-Cu(II) column to the PS-DVB column with 100 mM imidazole/0.5M NaCl, pH 7.0. The PS-DVB column was then washed with 5% acetonitrile-0.1% acetic acid, followed by on-line gradient elution from 5–50% acetonitrile with 0.1% acetic acid in 10 minutes through the ESI chip device and detected by the LCT mass spectrometer. An electrospray voltage of 1400V was applied to PS-DVB column. The LCT mass spectrometer was operated in the positive ion mode and mass spectral data were acquired using one-second ion integration times. As shown in FIG. 14, the two peptides (angiotensin I and angiotensin II) containing histidine residues in the five-peptide mixture were all captured and detected by mass spectrometer while the rest three peptides without histidine residues were washed out in the IDA-Cu(II) column and failed to be detected. For comparison, the mass spectrum of control sample containing 5-peptide mixture was shown in FIG. 13.

Figure 15:
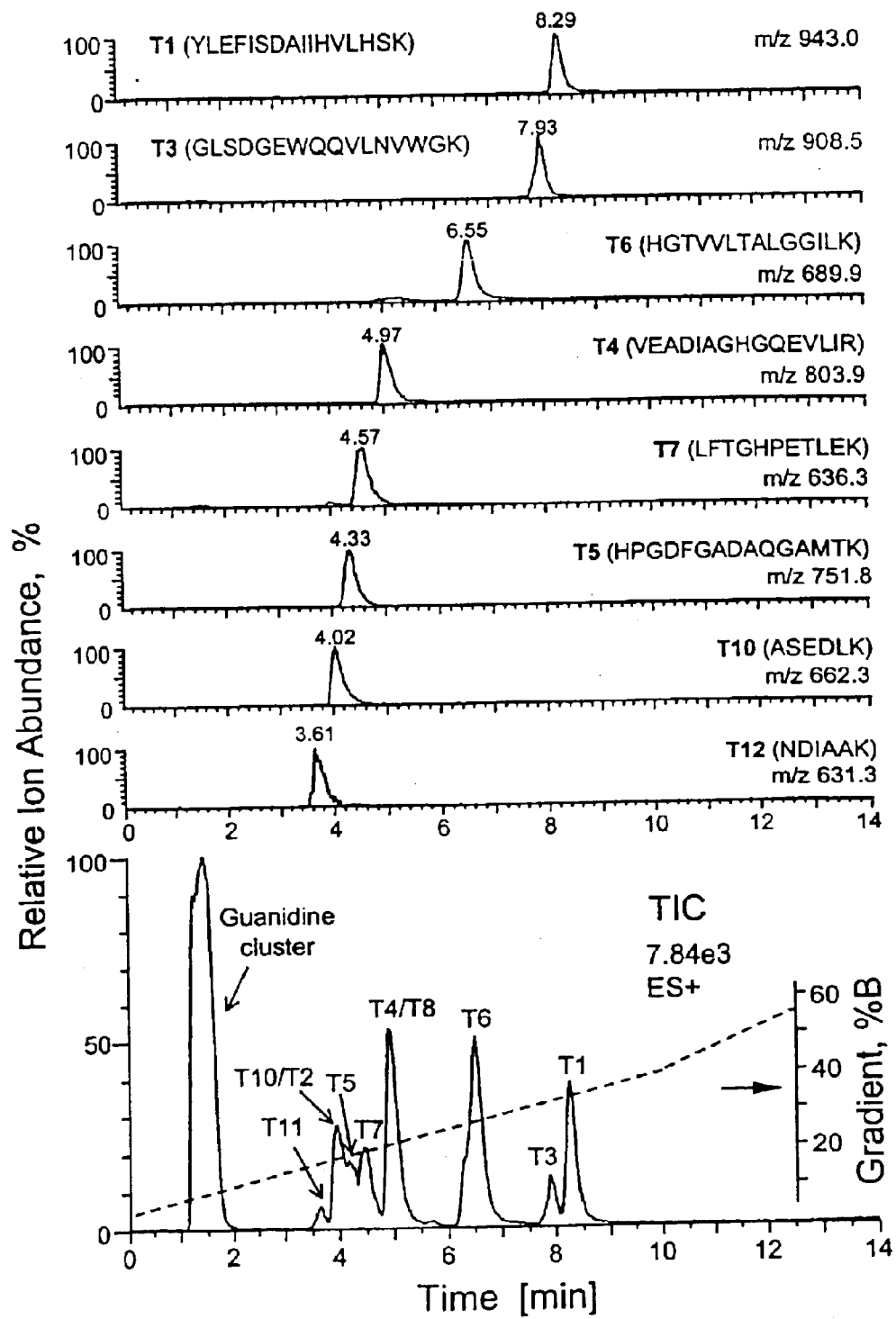
FIG. 15 shows a TIC chromatogram and extracted ion chromatograms from the LC-ESI-MS analysis of a 0.6 pmol of myoglobin tryptic digest on a stainless steel column (125 $\mu$m I.D.×10 cm) containing the PS-DVB-$C_{18}$ monolith coupled with a microchip electrospray device; mobile phase: A=0.1% v/v acetic acid and 0.01% v/v heptafluorobutyric acid in water, B=0.1% v/v acetic acid and 0.01% v/v heptafluorobutyric acid in acetonitrile. The gradient program was 0%→40%→70% in 0→10→15 min with flow rate 300 nL/min.

The copper chelates are also ideally suited for proteins such as horse heart myoglobin and lectins. The same column noted above is used for selectively binding myoglobin containing 4–5 surface histidines and consequent affinity separation of myoglobin from the mixture with peroxidase, cytochrome c, alphal-acid glycoprotein and chymotrypsinogen A. A similar condition as described above for the peptide mixture is used for loading and eluting the myoglobin followed by MS analysis. Alternatively, the bound myoglobin in IDA-Cu(II) monolith column can be carried out in situ (on-column) enzymatic digestion by loading the trypsin solution consisting of 50 mM ammonium biocarbonate pH 8.0 plus 10 mM DTT and 2 M Guanidine-HCl and incubating for 30–60 minutes. The resulting tryptic fragments were eluted to a stainless steel column (125 μm I.D.×10 cm) containing the PS-DVB-$C_{18}$ monolith with 100 mM imidazole/0.5M NaCl, pH 7.0. The PS-DVB-$C_{18}$ column was then washed with 0.1% acetic acid-0.01% heptafluorobutyric acid, followed by on-line gradient elution with 0%→40%→70% acetonitrile containing 0.1% acetic acid-0.01% heptafluorobutyric acid in 0→10→15 minutes through the ESI chip device and detected by the LCT-TOF mass spectrometer. The results shown in FIG. 15 reveal that the majority of myoglobin tryptic fragments has base line separation and detected coverage of myoglobin is more than 80%.

The ConA molecule is a widely-used lectin that is able to tightly bind to copper(II)-IDA functions of stationary phase. Therefore with the ConA loading to pre-charged Cu(II) column and serving as an adaptor, the glycosylation proteins can be separated from the mixture containing non-glycosylation analytes and identified by ESI/MS as described in detail in EXAMPLE 4. In order to obtain a ConA/Cu(II)-IDA column, a ConA solution (1 mg/mL) in 10 mM phosphate buffer, pH 7.0 is loaded on the Cu(II)-IDA column, the excess of ConA is washed away with 10 mM phosphate buffer, 100 mM NaCl pH 7.0. After separation of the interesting glycolated proteins, the ConA can be removed from the column either with eluents containing excess of competitive agents such as ammonium ions or glycine or with eluents of pH below 3.0.

3. Ni(II) ions are chelated to the aforementioned column for affinity separation of cloned HIS-tag proteins from the crude lysate of the cell. The copper ions in the column are removed by washing the column with excess of 50 mM EDTA solution. The column is then reloaded with nickel by treating the column with excess $NiCl_2$, followed by equilibration buffer with 20 mM sodium phosphate pH 7.0 and 0.2 M sodium chloride. A testing model sample, the *E coli* lysate containing the six-HIS tagged chorismate mutase/prephenate dehydrogenase at C-terminus (42,865 Da), is used for loading to the column. After the complete washing for non-specific binding proteins, the interest target protein is eluted with lowering the pH for the elution buffer. Consequently the above HIS-tagged protein is then purified and identified by ESI/MS. Alternatively, the bound HIS-tagged protein can be in situ digested by trypsin and the resulting tryptic fragments were eluted and identified by ESI/MS.

Figure 16:
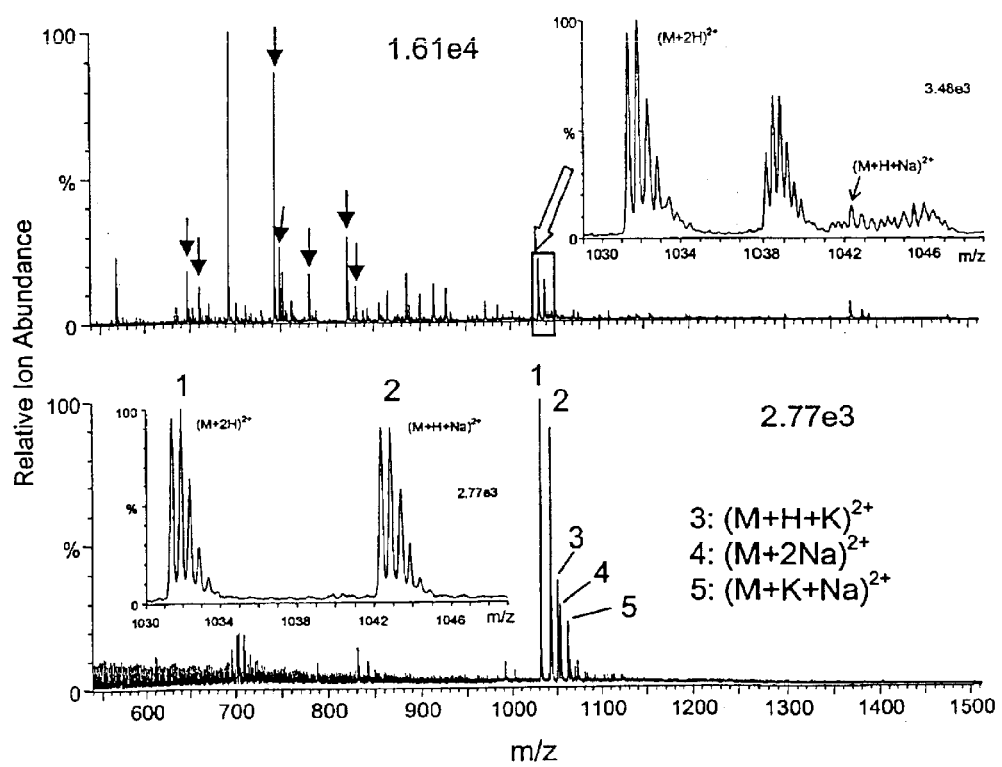
FIG. 16 shows a mass spectrum from the infusion of a beta-casein tryptic digest after affinity chromatography on a PEEK column (381 $\mu$m I.D.×4.7 cm) containing the monolithic IDA-Fe(III) stationary phase for separation of phosphopeptides. The top panel shows that the mass spectrum of 0.5 $\mu$M beta-casein tryptic digest in 50% methanol/50% water with 0.1% acetic acid through a microchip electrospray device over 1-min acquisition and serves as a control. The peaks indicated by arrow are the tryptic fragments of beta-casein. The inset, an expansion of the region between m/z 1030–1048, reveals the spectrum of a phosphopeptide (from beta-casein 48–61, FQpSEEQQQTEDELQDK) with monoisotopic mass 2060.8284 Da detected in control sample in a doubly charge state. The bottom panel shows that the mass spectrum of 10 pmol of beta-casein tryptic digest passed through the IDA-Fe(III) monolithic column, eluted by 2% $NH_4OH$ and re-suspended in 10 $\mu$L of 50% methanol/50% water with 0.1% acetic acid for infusion analysis through the microchip device. The inset displays that the doubly charged phosphopeptide ion has also Na adduction in addition to proton attachment.

4. Fe(III) or Ga(III) ions are chelated to the monolith IDA column for characterizing phosphorylation protein and peptides. The above monolith-Cu(II) column was used. The metal Cu(II) was stripped with 50 mM EDTA, pH 8.5. After completely washing column with water, the column was re-charged with 40 mM $FeCl_3$. After washing away excess metal ions with water, the column was equilibrated with loading solution (0.5% acetic acid). The tryptic digest of bovine beta-casein (10 pmol) was acidified with 1% acetic acid and loaded on the column. The column was then washed with 20% acetonitrile-0.1% acetic acid and followed by distilled water. The phosphopeptides were eluted with 50 μL of 2% ammonium hydroxide. After evaporation, the eluted sample was re-suspended in 10 μL of 50% methanol with 0.1% acetic acid for direct infusion analysis through the microchip device. The results (FIG. 16) demonstrated that after treated with monolith IDA-Fe(III) column, all non-phosphopeptides from beta-casein tryptic digest were washed out and only one phosphopeptide with a mass of 2060.8 was accumulated and detected by the mass spectrometer. A serious of adductions to this doubly charged ion by Na and K in addition to proton attachment was also detected in relatively abundant, consistent with the feature of phosphopeptides. Alternatively, prior to elution the bound phosphopeptides are treated with calf intestinal phosphatase (CIP) in the column. Then the dephosphopeptides are directly detected by ESI/MS or ESI/MS/MS. Comparison of the masses of the peptides and MS/MS data with and without CIP treatment, specific phosphorous sites can be determined.

EXAMPLE 4

This is the application of the device with affinity adsorbents including immobilized lectin (ConA) ligands prepared in EXAMPLE 1.

The immobilized ConA ligands in the attached capillary tube or/and chip reservoirs/channels are used for affinity capture of glycosylation proteins and peptides. Using the surface immobilized lectin (ConA) can eliminate the possible metal interaction of the ConA-Cu(II)-IDA to the glycosylated proteins. The device (including either the capillary column or chip reservoirs/channels or both) is initially equilibrated with 10 mM phosphate buffer, 100 mM NaCl pH 7.0, a mixture of 1 pmole of beta-lactoglobin, ribonuclease A, lysozyme, glucose oxidase is loaded into the column. The three above proteins without glycosylation are immediately eluted by the equilibration buffer and detected by mass spectrometer while glucose oxidase is adsorbed on the ConA stationary phase. Following an additional elution with 30% methanol-0.1% acetic acid, the glucose oxidase is eluted and detected by ESI/MS. Alternatively, the on-line trypsin and different glycosidases digestion for the bound glycosylated protein can provide additional information for the identification of glycosylated peptides as well as the glycosylted sites.

EXAMPLE 5

This is the application of the device with affinity adsorbents including immobilized antibodies prepared in EXAMPLE 2.

The device is used for detecting a biomarker in a diagnostic and forensic manner. The initial test is conducted by immobilizing polyclonal rabbit anti-human lactoferrin antibody in the device. The commercially available antibody can be further purified through protein A or protein G column. The immobilized polyclonal rabbit anti-human lactoferrin antibody in the device (either in the attached capillary column or in chip reservoirs/channels or both) is equilibrated with 20 mM phosphate, 0.15 M NaCl pH 7.0. The purified human lactoferrin (1 pmole) is directly injected to the device or sparked into a plasma or urine sample for injection to the device. After complete wash with the loading buffer followed by 5 mM ammonium acetate pH 7.0, the elution buffer containing 0.1% acetic acid-30% methanol is applied for eluting the human lactoferrin, detected by ESI/MS. Practically, for the detection of any biomarker analyte by the aforementioned device, the commercial available secondary antibody, for instance sheep anti-rabbit IgG, protein A, protein G, is immobilized on the device as a universal immobilized antibody for identifying the analytes. In this case, the primary antibody against the interesting analyte is loaded to the device first using the loading buffer, followed by the sample loading and elution as described above for the ESI/MS identification. Alternatively, more than one of the different primary antibodies can be loaded to the different row or column reservoirs of the micro chip, the device can be used for multiple analyses of the analytes.

EXAMPLE 6

The device with affinity adsorbents including immobilized enzyme prepared in EXAMPLE 2 is used for on-line digestion, sample cleanup and further identification by ESI/MS. In the device, the attached capillary column is immobilized with trypsin, a member of proteases, while the chip array is immobilized with a hydrophobic stationary phase in its reservoirs/channels.

The capillary column is equilibrated with 50 mM ammonium bicarbonate pH 8.0, 10 mM DTT and 4 M urea. A purified cytochrome c sample (1 pmole) is loaded into the column for 5 min at room temperature. The digested peptides are then eluted to the chip reservoir adsorbent with 5 mM ammonium acetate pH 7.0, where the peptides are bound on the hydrophobic adsorbent for sample cleanup. The tryptic fragments of cytochrome c are finally eluted with an aqueous solution containing 50%(v/v) methanol and 0.1% acetic acid, and detected by ESI/MS.

EXAMPLE 7

In situ enzymatic and chemical treatment for the bound analytes produces an additional method for on-line characterizing of the analytes. When the analyte is bound in the capillary column through metal interactions such as myoglobin and bovine beta-casein in EXAMPLE 3 or through glycosylation interaction such as glucose oxidase in EXAMPLE 4, the bound proteins can be further treated with trypsin by loading the trypsin solution (50 mM ammonium bicarbonate pH 8.0, 10 mM DTT and 4 M urea) into the column for on-column digestion. The resulting tryptic fragments are then eluted either to a second PS-DVB-$C_{18}$ column for gradient elution in order to achieve the efficient separation (see FIG. 15) or directly to the chip reservoirs containing a hydrophobic stationary phase with 5 mM ammonium acetate, pH 7.0, for sample cleanup and followed by elution for the ESI/MS identification of the tryptic fragments as described in EXAMPLE 6. The other enzymes such as CIP and glycosidases can also be applied for removing and further identifying the bound phosphorylated or glycosylated peptides as described in EXAMPLE 3 and 4 respectively.

EXAMPLE 8

The present device is used for two-dimensional affinity separation by combining the adsorption, enzymatic modification on the bound analytes and desorption between the micro column platform and microchip platform. For instance, the protein bound in the column through metal interaction can be enzymatically treated with trypsin and eluted to a chip array containing a hydrophobic stationary phase for sample cleanup to make it possible for on-line separation, sample cleanup and mass detection as described in EXAMPLE 7. Alternatively, the combination of Cu(II) charged micro column for histidine surface proteins and Con A immobilized microchip reservoir for glycosylation proteins can fraction only the histidine-rich glycoproteins from the mixture samples. Additional 2-D affinity separation can also be conducted by combining both Fe(III) charged column and ConA loaded a micro chip reservoir/channel for proteins and peptides with both phosphorylation and glycosylation modifications.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for analysis comprising:
   providing an electrospray device comprising:
   a substrate having:
   a) an injection surface,
   b) an ejection surface opposing the injection surface, wherein the substrate has at least one spray unit which comprises:
   an entrance orifice on the injection surface,
   an exit orifice on the ejection surface,
   a channel extending through the substrate between the entrance orifice and the exit orifice, and
   a recess extending into the ejection surface and surrounding the exit orifice, c) polymerized separation material comprising affinity chromatographic adsorbent, wherein the separation material is associated with said electrospray device at a location suitable to effect chromatographic separation of analytes passing through said electrospray device, and d) an electric field generating source positioned to define an electric field surrounding at least one exit orifice; and selectively immobilizing affinity ligands on the polymerized separation material of the device.

2. The method of claim 1, wherein said affinity chromatographic adsorbent comprises an immobilized metal ion chelating ligand.

3. The method of claim 2, wherein said immobilized metal ion chelating ligand comprises iminodiacetic acid, nitrilo triacetic acid, or tris(carboxymethyl) ethylene diamine.

4. The method of claim 1, wherein said affinity chromatographic adsorbent comprises an immobilized ligand molecule comprising an organic compound, fatty acid, inhibitor, protein, peptide, enzyme, coenzyme, receptor, affinity tag, nucleic acid, antibody, biotin, avidin, carbohydrate, lectin, dye, or protein surface domain involved in molecular recognition.

5. The method of claim 4, wherein said immobilized ligand molecule comprises a potential drug candidate or a mixture with potential drug candidates from a combinatorial compound library, beazamidine, D-biotin, biotinylated molecules, Avidin, Protein A, antisense peptides, antisense Arg-vasopressin peptide, trypsin, adenosine 5'-monophosphate (5'-AMP), Interleukin-2 receptor, polyamino acids, polyhistidine, histidine, lysine, a fragment of calf thymus DNA, sheep anti-rabbit IgG, monosaccharide, monosaccharide derivative, concanavalin A, or Cibacron Blue F3G-A.

6. The method of claim 1, wherein said device further comprises a micro column in fluid communication with said polymerized separation material and having an affinity chromatographic adsorbent within said micro column, said method further comprising selectively immobilizing affinity ligands on the polymerized separation material within said micro column.

7. The method of claim 6, wherein said affinity chromatographic adsorbent within said micro column comprises an immobilized metal ion chelating ligand.

8. The method of claim 7, wherein said immobilized metal ion chelating ligand comprises iminodiacetic acid, nitrilo triacetic acid, or tris(carboxymethyl) ethylene diamine.

9. The method of claim 6, wherein said affinity chromatographic adsorbent comprises an immobilized ligand molecule comprising an organic compound, fatty acid, inhibitor, protein, peptide, enzyme, coenzyme, receptor, affinity tag, nucleic acid, antibody, biotin, avidin, carbohydrate, lectin, dye, or protein surface domain involved in molecular recognition.

10. The method of claim 9, wherein said immobilized ligand molecule comprises a potential drug candidate or a mixture with potential drug candidates from a combinatorial compound library, benzamidine, D-biotin, biotinylated molecules, Avidin, Protein A, antisense peptides, antisense Arg-vasopressin peptide, trypsin, adenosine 5'-monophosphate (5'-AMP), Interleukin-2 receptor, polyamino acids, polyhistidine, histidine, lysine, a fragment of calf thymus DNA, sheep anti-rabbit IgG, monosaccharide, monosaccharide derivative, concanavalin A, or Cibacron Blue F3G-A.

11. A method for analysis comprising:

providing the electrospray device according to claim 1, said electrospray device further comprising an array of multiple injection surfaces in fluid communication with a respective one of an array of multiple exit orifices through a channel and a capillary tube in fluid communication with an injection surface, wherein at least one of the injection surface/channel and capillary tube contain at least one immobilized affinity chromatographic adsorbent;

selectively binding an analyte on said affinity chromatographic adsorbent by affinity capture;

optionally, performing chemical, enzymatic, or physical treatment of said immobilized analyte;

selectively desorbing said analyte;

electrospraying said desorbed analyte; and passing said electrosprayed analyte to a detector.

12. The method of claim 11, wherein said affinity chromatographic adsorbent comprises an immobilized metal ion chelating ligand.

13. The method of claim 12, wherein said immobilized metal ion chelating ligand comprises iminodiacetic acid, nitrilo triacetic acid, or tris(carboxymethyl) ethylene diamine.

14. The method of claim 11, wherein said affinity chromatographic adsorbent comprises an immobilized ligand molecule comprising an organic compound, fatty acid, inhibitor, protein, peptide, enzyme, coenzyme, receptor, affinity tag, nucleic acid, antibody, biotin, avidin, carbohydrate, lectin, dye, or protein surface domain involved in molecular recognition.

15. The method of claim 14, wherein said immobilized ligand molecule comprises a potential drug candidate or a mixture with potential drug candidates from a combinatorial compound library, benzamidine, D-biotin, biotinylated molecules, Avidin, Protein A, antisense peptides, antisense Arg-vasopressin peptide, trypsin, adenosine 5'-monophosphate (5'-AMP), Interleukin-2 receptor, polyamino acids, polyhistidine, histidine, lysine, a fragment of calf thymus DNA, sheep anti-rabbit IgG, monosaccharide, monosaccharide derivative, concanavalin A, or Cibacron Blue F3G-A.

16. The method of claim 11, wherein said device comprises a micro column and has an affinity chromatographic adsorbent within said micro column, said method further comprises selectively binding an analyte on said affinity chromatographic adsorbent within said micro column by affinity capture.

17. The method of claim 11, further comprising performing multiple analyses of one or more analytes, including at least one of affinity binding, chemical, enzymatic, and physical modifications of the analytes.

18. The method of claim 11, wherein said affinity binding, chemical, enzymatic, or physical modification, and elution of the analytes is carried out in a two-dimensional mode.

19. The method of claim 11, wherein said detector is a mass spectrometer.

* * * * *